United States Patent [19]
Moineau et al.

[11] Patent Number: 5,925,388
[45] Date of Patent: Jul. 20, 1999

[54] ISOLATED DNA ENCODING ENZYME FOR PHAGE RESISTANCE

[75] Inventors: Sylvain Moineau, Bradenton, Fla.; Shirley A. Walker, Raleigh, N.C.; Ebenezer R. Vedamuthu, Bradenton; Peter A. Vandenbergh, Sarasota, both of Fla.

[73] Assignee: Quest International Flavors & Food Ingredients Company, Bridgewater, N.J.

[21] Appl. No.: 08/820,980

[22] Filed: Mar. 19, 1997

Related U.S. Application Data

[60] Division of application No. 08/424,641, Apr. 19, 1995, which is a continuation-in-part of application No. 08/366,480, Dec. 30, 1994, abandoned.

[51] Int. Cl.$^6$ .............................. A23C 9/13; C12N 15/87
[52] U.S. Cl. ..................... 426/43; 435/172.3; 435/252.3
[58] Field of Search .............................. 435/172.3, 252.3; 426/43

[56] References Cited

PUBLICATIONS

Mercenier, A. et al. "Genetics of *Streptoccus thermophilus*: a review" Journal of Dairy Science (Dec. 1989), vol. 72, No. 12, pp. 3444–3454.

Nyengaard, N. et al. "LlaAl and LlaBl, two type–II restriction endonucleases from *Lactoccus lactis* subsp. cremoris W9 and W56 recognizing, respectively, 5'–/GATC–3' and 5'–C/TRY AG–3'" Gene (Dec. 22, 1993), vol. 136, No. 1–2, pp. 371–372.

*Primary Examiner*—Kawai Lau
*Attorney, Agent, or Firm*—Ian C. McLeod

[57] ABSTRACT

An isolated DNA of a *Lactococcus lactis* showing a SEQ ID NO:1 encoding a restriction and twp modification enzymes (R/M SEQ ID NO: 2, 3 and 4). The isolated DNA is used to transform sensitive dairy cultures, such as *Lactococcus lactis* and *Streptococcus thermophilus*, to provide phage resistance. *Escherichia coli* can be used to produce endonucleases.

14 Claims, 11 Drawing Sheets

1  2  3  4

```
1    CGAGCTTTCTAATGCTTAGTGCTTTAAGATTAGGATAGCACGACTTATTT
51   ATTTTCCAATGAAATTAACTAGCAATTCGGGTATAATATATTTATGAATT
                                                  M  N  L
101  TATTACAAAAAAACAAGATCAACTTACGTCCGTTTACTAAATGGACAGGT
      L  Q  K  N  K  I  N  L  R  P  F  T  K  W  T  G
151  GGGAAAAGGCAACTACTGCCACACATTCAATACCTAATGCCAGAAAAATA
      G  K  R  Q  L  L  P  H  I  Q  Y  L  M  P  E  K  Y
201  CAATCATTTTTTCGAACCTTTTATTGGTGGTGGCGCTTTGTTTTTTGAAC
       N  H  F  F  E  P  F  I  G  G  G  A  L  F  F  E  P
251  CCGCTCCTCAAAAAGCAGTTATTAACGACTTCAATTCTGAGCTTATAAAC
      A  P  Q  K  A  V  I  N  D  F  N  S  E  L  I  N
301  TGTTACCGGCAGATGAAAGATAATCCTGAGCAATTGATAGAATTGTTGAC
      C  Y  R  Q  M  K  D  N  P  E  Q  L  I  E  L  L  T
351  TAATCATCAGCGGGAAAATTCTAAAGAATATTATTTAGACTTACGTTCTT
      N  H  Q  R  E  N  S  K  E  Y  Y  L  D  L  R  S  S
401  CTGATAGAGATGGAAGAATTGATAAGATGAGCGAAGTTGAACGTGCTGCT
       D  R  D  G  R  I  D  K  M  S  E  V  E  R  A  A
451  AGAATTATGTATATGCTACGTGTTGATTTTAATGGTTTATATCGTGTTAA
      R  I  M  Y  M  L  R  V  D  F  N  G  L  Y  R  V  N
501  TTCGAAAAACCAGTTTAATGTGCCTTATGGAAGATATAAAAATCCTAAGA
       S  K  N  Q  F  N  V  P  Y  G  R  Y  K  N  P  K  I
551  TAGTTGATAAAGAATTGATTGAAAGTATTTCCGAGTACTTGAATAACAAT
         V  D  K  E  L  I  E  S  I  S  E  Y  L  N  N  N
601  TCTATTAAGATCATGAGTGGAGATTTTGAAAAAGCCGTTAAAGAAGCACA
      S  I  K  I  M  S  G  D  F  E  K  A  V  K  E  A  Q
651  GGATGGAGATTTTGTTTATTTCGACCCTCCATACATTCCACTTTCTGAAA
       D  G  D  F  V  Y  F  D  P  P  Y  I  P  L  S  E  T
701  CTAGCGCCTTTACTTCTTATACACACGAAGGCTTTAGCTACGAAGATCAA
        S  A  F  T  S  Y  T  H  E  G  F  S  Y  E  D  Q
751  GTTAGGCTAAGAGATTGTTTCAAACAGTTAGATTCAAAAGGGGTATTCGT
      V  R  L  R  D  C  F  K  Q  L  D  S  K  G  V  F  V
801  CATGCTTTCAAATTCTTCAAGCCCTTTAGCGGAGGAATTATATAAAGATT
       M  L  S  N  S  S  S  P  L  A  E  E  L  Y  K  D  F
851  TTAACATCCATAAAATTGAAGCTACTCGAACAAATGGGGCTAAATCATCT
      N  I  H  K  I  E  A  T  R  T  N  G  A  K  S  S
901  AGTCGTGGAAAAATCACTGAAATCATCGTAACCAATTATGGCAATTAACG
      S  R  G  K  I  T  E  I  I  V  T  N  Y  G  N  *
                                                   M  A  I  N  E
```

FIG. 4A

```
 951  AATATAAGTATGGAGGTGTTTTAATGACAAAACCATACTATGAAAAAGAA
        Y  K  Y  G  G  V  L  M  T  K  P  Y  Y  E  K  E

1001  AACGCAATTCTCGTTCACGCAGATTCATTTAAATTATTAGAAAAAATTAA
        N  A  I  L  V  H  A  D  S  F  K  L  L  E  K  I  K

1051  ACCTGAAAGCATGGACATGATATTTGCTGACCCTCCTTACTTTTTAAGTA
        P  E  S  M  D  M  I  F  A  D  P  P  Y  F  L  S  N

1101  ATGGAGGAATGTCAAATTCAGGTGGTCAAATTGTTTCTGTTGATAAAGGG
        G  G  M  S  N  S  G  G  Q  I  V  S  V  D  K  G

1151  GATTGGGATAAAATTTCTTCATTTGAAGAAAAACATGACTTTAATAGACG
        D  W  D  K  I  S  S  F  E  E  K  H  D  F  N  R  R

1201  TTGGATTAGGTTAGCAAGATTGGTTTTAAAACCCAACGGAACTATTTGGG
        W  I  R  L  A  R  L  V  L  K  P  N  G  T  I  W  V

1251  TTTCCGGAAGCCTTCATAACATATATTCTGTCGGGATGGCGCTGGAACAG
        S  G  S  L  H  N  I  Y  S  V  G  M  A  L  E  Q

1301  GAAGGTTTCAAAATCTTAAATAATATAACTTGGCAAAAGACAAATCCTGC
        E  G  F  K  I  L  N  N  I  T  W  Q  K  T  N  P  A

1351  ACCTAATCTATCATGTCGGTACTTCACCCACTCTACAGAGACAATTTTAT
        P  N  L  S  C  R  Y  F  T  H  S  T  E  T  I  L  W

1401  GGGCAAGAAAGAACGATAAAAAATCTCGCCATTATTATAACTATGAATTG
        A  R  K  N  D  K  K  S  R  H  Y  Y  N  Y  E  L

1451  ATGAAAGAGTTTAATGACGGGAAACAAATGAAAGATGTTTGGACAGGTAG
        M  K  E  F  N  D  G  K  Q  M  K  D  V  W  T  G  S

1501  TCTGACAAAAAAATCAGAAAAATGGGCTGGGAAACATCCAACTCAGAAGC
        L  T  K  K  S  E  K  W  A  G  K  H  P  T  Q  K  P

1551  CAGAGTATATTTTAGAACGGATAATCTTAGCTAGTACAAAGGAAAATGAT
        E  Y  I  L  E  R  I  I  L  A  S  T  K  E  N  D

1601  TATATTTTAGACCCTTTCGTCGGAAGTGGAACTACTGGTGTAGTAGCCAA
        Y  I  L  D  P  F  V  G  S  G  T  T  G  V  V  A  K

1651  GAGATTGGGGCGTAAATTTATTGGGATTGATTCTGAGAAAGAATATCTTA
        R  L  G  R  K  F  I  G  I  D  S  E  K  E  Y  L  K

1701  AAATTGCTAAAAAAAGGCTAAATAAAGGAGCAACATATGGACTTTAATAA
        I  A  K  K  R  L  N  K  G  A  T  Y  G  L  *
                                        M  D  F  N  N

1751  TTACATCGGTTTAGAATCTGACGATAGATTAAATGCTTTTATGGCAACAC
        Y  I  G  L  E  S  D  D  R  L  N  A  F  M  A  T  L

1801  TTTCCGTAACTAATAGAACTCCCGAATACTACGTGAACTGGGAAAAAGTT
        S  V  T  N  R  T  P  E  Y  Y  V  N  W  E  K  V

1851  GAACGTGAAACACGAAAATTTGAATTAGAACTAAATACTTTAAACTATCT
        E  R  E  T  R  K  F  E  L  E  L  N  T  L  N  Y  L
```

FIG. 4B

```
1901  CATTGGGAAAGAAGATATTTATAGTGAAGCACTTGAACTATTTACCAATC
       I  G  K  E  D  I  Y  S  E  A  L  E  L  F  T  N  Q

1951  AACCTGAATTGCTTAAAGCTATTCCTAGTTTGATTGCTAGTAGAGATACA
       P  E  L  L  K  A  I  P  S  L  I  A  S  R  D  T

2001  TCTTTAGATATACTAAACATTGACGAAAATGATGATATGAGTTTTGAACA
       S  L  D  I  L  N  I  D  E  N  D  D  M  S  F  E  Q

2051  ACTTAACTTTCTTGTTATCGACGAAAATTGTATCGCTGATTATGTAGACT
       L  N  F  L  V  I  D  E  N  C  I  A  D  Y  V  D  F

2101  TTATTAACCAGGCAGGTTTACTAGATTTTCTACAGAATAAAGCAAAACGT
       I  N  Q  A  G  L  L  D  F  L  Q  N  K  A  K  R

2151  TCTCTGGTAGACTATGTGTATGGTGTTGAAGCAGGGCTTGATAGCAATGC
       S  L  V  D  Y  V  Y  G  V  E  A  G  L  D  S  N  A

2201  TCGAAAAAACCGAAGCGGTACAACCATGGAGGGGATTTTAGAACGTACTG
       R  K  N  R  S  G  T  T  M  E  G  I  L  E  R  T  V

2251  TTTCAAAAATAGCTCAAGAGAAAGGGCTTGAATGGAAGCCACAGGCAACC
       S  K  I  A  Q  E  K  G  L  E  W  K  P  Q  A  T

2301  GCTTCTTTTATCAAGTCTCAATGGGACATAGAAGTCCCTGTAGATAAATC
       A  S  F  I  K  S  Q  W  D  I  E  V  P  V  D  K  S

2351  AAAAAGACGCTTTGATGCAGCAGTTTACTCTCGTGCGCTCAATAAGGTTT
       K  R  R  F  D  A  A  V  Y  S  R  A  L  N  K  V  W

2401  GGCTCATAGAAACAAATTACTACGGCGGTGGAGGAAGTAAACTCAAAGCA
       L  I  E  T  N  Y  Y  G  G  G  G  S  K  L  K  A

2451  GTTGCTGGAGAATTTACAGAATTGAGTCAGTTTGTAAAAACATCAAAAGA
       V  A  G  E  F  T  E  L  S  Q  F  V  K  T  S  K  D

2501  TAATGTTGAATTTGTATGGGTAACAGACGGCCAAGGGTGGAAATTTTCCC
       N  V  E  F  V  W  V  T  D  G  Q  G  W  K  F  S  R

2551  GCTTACCACTTGCAGAAGCTTTCGGACACATCGATAACGTTTTCAATCTA
       L  P  L  A  E  A  F  G  H  I  D  N  V  F  N  L

2601  ACCATGTTGAAAGAAGGTTTCTTATCTGATTTATTCGAAAAAGAAATTTA
       T  M  L  K  E  G  F  L  S  D  L  F  E  K  E  I  *

2651  AAAAGACAGAGAATCTCTGTCTTTTTAAATTTCAATTCCTTCCTTCTGCT
2701  AGCTATAACTTTCCAAAAAACCTGAAAAACGGTTCTGTTGCAATTGTATG
2751  TGGGGTCGGAACTTACTACTATATCATGAGAAATGAAGATTAAAGTTGAA
2801  ACAAAAAAACAGATTATTTTAAAATGTAAATCTGTTTTTGTTTGGGCTGA
2851  TTTTATCACACCAATTCTATGTTCAGAAAATGGTCATTTTCTGGACACTC
2901  TTCTTTTGTTATTAAAACTCTCAAAATCATTTACATTTATTGTTCATTAA
2951  CCCGTAATTTATTCTATGTTCATTTATAGATATC
```

FIG. 4C

```
                                                                                           Motif I
                        *   ***  ****  **   *           **             *       ***  *
M.LlaIIA    MNLLQKNKINLRPFTKWTGGKRQLLPHIQYLMPE--KYNHF--FEPFIGGALFF-----EPAPQKAVINDFNSELINC    70
M.DpnII     MKIKEIKKVTLQPPTKWTGGKRQLLPVIRELIPKTYNRY----FEPFVGGGALFF-----DLAPKDAVINDFNAELINC    70
M.MboA                 MKPFIKWAGGKNSLLDEIQKRLPDFVHSQDFCLVEPFVGGAVSLWALSDLPHLKQLVINDCNADLINV    69
Dam                    MKKNRAPLKWAGGKYPLLDDIKRHLP---KGE--CLVEPFVGAGSVFL-----NTDFSRYILADINSDLISL    62

*                     *          *                      *     ***  *   ***
M.LlaIIA    YRQMKDNPEQLIELLTN--HQRENSKEYYLDLRSS-------DRDGRIDKMS--EVERAARIMMLRVDFNGLYRVNSKNQPNV   143
M.DpnII     YQQIKDNPQELIEILKV--HQEYNSKEYYLDLRSA-------DRDERIDMMS--EVQRAARILYMLRVNFNGLYRVNSKNQPNV   143
M.MboA      YQVIKNNPDDLIGYIEN--LQSHYDKLTDLESKKPYFYHKRDVFNQRTSNDIEQAGLFIFLNKSAFNGLYRVNKNNQPNV   147
Dam         YNIVKMRTDEYVQAARELFVPETNCAEVYYQF---------REEFNKSQD--PFRRAVLFLYLNRYGYNGLCRYNLRGEPNV   133

Motif II
               *  ***            *    *                *  **  *  *  **    *        *
M.LlaIIA    PYGRYKNPKIVDKELIESISEYLNNNSIKIMSGDFEKAVKEAQDG--DFVYFDPPYIPLSETSAPTSYTHEGPSYEDQ   219
M.DpnII     PYGRYKNPKIVDEELISAISVYINNNQLEIKVGDFEKAIVDVRTG--DFVYFDPPYIPLSETSAPTSYTHEGPSFADQ   219
M.MboA      PIGNYKPTFVDKENILNISKKLQN--TKILSGDFELVLAHLPNNFPCLFYLDPPYRPISDTASPTSYSDNGFDDNEQ   223
Dam         PFGRYKKPYFPEAELYH--FAE--KAQNAFFYCESYADSMARADDA--SVVYCDPPYAPLSATANFTAYHTNSPTLEQQ   206

*
M.LlaIIA    VRLRDCFKQLDSKGVFVMLS------NSSSPLAEELYKDFNIHKIEATRTNGAKSSSRGKITEIIVTNYGN   284
M.DpnII     VRLRDAFKRLSDTGAYVMLS------NSSSALVEELYKDFNIHYVEATRTNGAKSSSRGKISEIIVTNYEK   284
M.MboA      KRLANFCKKIDKLGHYFLLSNSDPKNTNSSDEFFDELYQDFKIERIQANRTISANSNGRKKVNEIIVSNGV   294
Dam         AHLAEIAEGLVERHIPVLIS------NHDTMLTREWYQRAKLHVVKVRRSISSNGGTRKKVDELLALYKPGVVSPAKK   278

FIG. 5A
```

```
                                                                  Motif II
              *                        *      *********              *           *  ***
M.LlaIIB    MAINEYKYGGVLMTKPYYEKENA--ILVHADSFKLLEKIKPESMDMIFADPPYPL-SNGGMSNSGGQIVSVDKGDWDK    75
M.DpnA      MKNNEYKYGGVLMTKPYYNKNKM--ILVHSDTFKFLSKMKPESMDMIFADPPYPL-SNGGISNSGGQVVSVDKGDWDK    75
M.MboC         MRIKPYFESDDKNFNIYQGNCIDFMSHFQDNSIDMIFADPPYFL-SNDGLTFKNSIIQSVNKGEWDK              66
M.HinfI        MMKENINDFL-NTILKG-DCIEKLKTIPNESIDLIFADPPYFMQTEGKLLRTNGDEFSGVDDEWDK               64

*            *     *          *          **     **     *  *
M.LlaIIB    ISSFEEKHDFNRRWIRLARLVLKPNGTIWVSGSLHNIYSVGMALEQEGFKILNNITWQKTNPAPNLSCRYPTHSTET  152
M.DpnA      ISSFEEKHEPNRKWIRLAKEVLKPNGTVWISGSLHNIYSVGMALEQEGFKILNNITWQKTNPAPNLSCRYPTHSTET  152
M.MboC      NDNEASIYNFNHEWIAQARQLLKDNGTIWISGTHHNIFTVGVLKENNFKILNIITWEKPNPPPNFSCRYPTYSSEW   143
M.HinfI     FNDFVEYDSPCELWLKECKRILKSTGSIWVIGSFQNIYRIGYIMQNLDFWILNDVIWNKTNPVPNFGGTRFCNAHET  141

*         *                           **       ****            *   ****
M.LlaIIB    ILWARKNDKKSRHYYNYELMKEFNDGKQMKDVWTGSLTKKSEKW---AGK--HPTQKPEYILERIILASTKENDYIL  224
M.DpnA      ILWARKNDKKARHYYNYDLMKELNDGKQMKDVWTGSLTKKVEKW---AGK--HPTQKPEYLLERIILASTKEGDYIL  224
M.MboC      IIWARKH-SKIPHYFNYDLMRKLNGDKQQKDIWRLPAVGSWEKT---QGK--HPTQKPLGLLSRIILSSTQKDDLIL  214
M.HinfI     MLWCSKC-KKNKFTFNYKTMKHLNQEKQERSVWSLSLCTGKERIKDEEGKAHSTQKPESLLYKVILSSSKPNDVVL   217
                 Motif I
              ****  ****                    *   *       *
M.LlaIIB    DPFVGSGTTGVVAKRLGRKFIGIDSEKEYLKIAKKRLNKGATYGL                                   269
M.DpnA      DPFVGSGTTGVVAKRLGRRFIGIDAEKEYLKIARKRLEAENETN                                    268
M.MboC      DPFSGSGTTGIAGVLLDRNYIGIEQELEFLELSKRRYHEITPVLKNEFKQKIRKQISAI                     273
M.HinfI     DPFFGTGTTGAVAKALGRNYIGIEREQKYIDVAEKRLREIKPNPNDIELLSLEIKPPKVPMKTLIEADFL          287
```

FIG. 5B

```
R.LlaII   MDFNNYIGLESDDRLNAFMATLSVTNRTPEYYVNWEKVERETRKFELELNTLNYLIGKEDIYSEALELFTNQPELLKAI      79
R.DpnII         MKQTRNFDEWLSTMTDTVADWTYTDFPKVYKNVSSIKVALNIMNSLIGSKNIQEDFLDLYQNYPEILKVV      71
R.MboI            MKLAFDDFLNSMSETNTTLDYFTDFDKVKKNVAQIEIHLNQLNYLLGKDDLKQAVYDLYAECPNAFSIL      69
                ***   *            *        *                    *      *   *
R.LlaII   PSLIASRDTSLDILNIDENDDMSFEQLNFLVIDENCIADYVDFINQAGLLDFLQNKAKRSLVDYVGVEAGLDSNAR     156
R.DpnII   PLLIAKRLRDTIIVK-DPIKDFYFD----FSKRNYSIEEYTMFLEKSGIFDLLQNHLVSNLVDYTGVEVGMDTNGR     143
R.MboI    EILIAVRKKE-QKKSLDEKGQVVTLNSYF-----QSADKIIDFLNNTGLADVFRDKNIKNLVDYVFGIEVGLDTNAR     140
          *** *       *                  *                         ** ***     **    **
R.LlaII   KNRSGTTMEGILERTVSKIAQEKGLEWKPQATASFIKSQWDIEVPV-----DKSKRRPDAAVYSRALNKVWLIETNYYG    230
R.DpnII   KNRTGDAMENIVQSYLEAEGYILGENLFKEIEQNEIEEIFSVDLSAITNDGNTVKRPDFVI--KNEQVLYLIEVNFYS    219
R.MboI    KNRGGDNM----SKAVQLLFDNADIYYKKEVRNTIFT---DIE-SL----GADVKQPDFVI--KTKRKTYVIETNYYN    204
          ***                 *                                 * *     ******
R.LlaII   GGGSKLKAVAGEFTELSQFVKTSKDNVEPVWVTDGQGWKFSRLPLAEAFGHIDNVFNLTMLKEGFLSDLFEKEI       304
R.DpnII   GSGSKLNETARSYKMIAEETKAI-PNVEFMWITDGQGWYKAKNNLRETFDILPFLYNINDLEHNILKNLK           288
R.MboI    SGGSKLNEVARAYTDVAPKINQYSQ-YEFVWITDGQGWKTAKNKLQEAYTHIPSVYNLYTL-HGFIEQLNSEGVIKDW    280
          ****                        *  ********
```

FIG. 5C

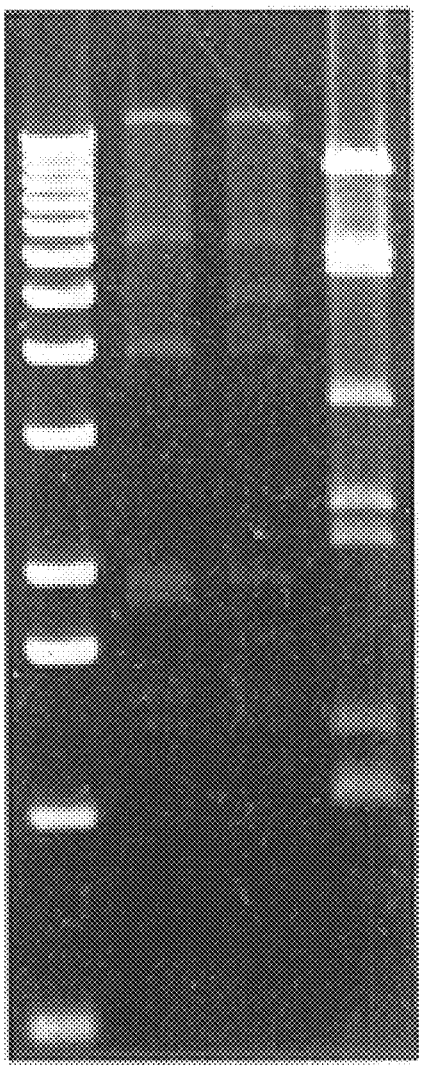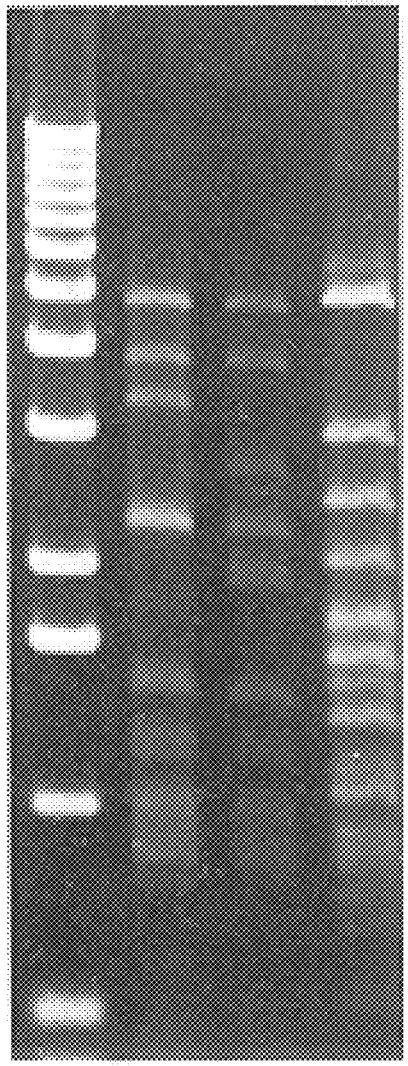
FIG. 6

ISOLATED DNA ENCODING ENZYME FOR PHAGE RESISTANCE

This is a divisional of application Ser. No. 08/424,641 filed on Apr. 19, 1995 which is a continuation-in-part of 08/366,480 filed Dec. 30, 1994, now abandoned.

BACKGROUND OF THE INVENTION

(1) Field of the Invention

The present invention relates to transformed dairy cultures with a natural 7.8-kb plasmid pSRQ700 which was isolated from *Lactococcus lactis* subsp. cremoris DCH-4, a known strain. pSRQ700 encodes a restriction/modification system named LlaII. When introduced into a phage-sensitive dairy culture, such as *L. lactis*, pSRQ700 confers strong phage resistance against the three most common lactococcal phage species: 936, c2 and P335 found in dairy product fermentations. The LlaII endonuclease was purified and found to cleave the palindromic sequence 5'/GATC-3'. The low copy plasmid pSRQ700 was mapped and the genetic organization of LlaII localized. Cloning and sequencing of the entire LlaII system allowed the identification of three open reading frames. The three genes (LlaIIA, LlaIIB, and LlaIIC) overlapped and are under one promoter. A terminator was found at the end of LlaIIC. The genes LlaIIA and LlaIIB coded for $m^6A$-methyltransferases and LlaIIC for an endonuclease. The native LlaII R/M system from *Lactococcus lactis* is also expressed by and conferred strong phage resistance to various industrial *S. thermophilus* strains. Resistance was observed against phages isolated from yogurt and Mozzarella wheys. This is the first demonstration of increased phage resistance in *S. thermophilus*.

(2) Description of Related Art

*Lactococcus lactis* and *Streptococcus salivarius* subsp. *thermophilus* cultures are used extensively worldwide in the manufacture of fermented dairy products. The cultures are normally inoculated into pasteurized or heat-treated milk to quickly start and control the fermentation. In this non-sterile milk environment, the added cells come into contact with the wild bacteriophage population that has survived pasteurization. Although natural phage concentration is low, their population increases very rapidly if phage-sensitive cells are present in the starter culture. The consequent lysis of a large number of sensitive cells retards the fermentation process. To cope with this natural phenomenon, the dairy industry has developed a series of solutions including the use of phage resistant *Lactococcus lactis* strains (Hill, C., FEMS Microbiol. Rev. 12:87–108 (1993)).

*Lactococcus lactis*

In the last decade, extensive research was conducted on interactions between lactococcal phage and their hosts. *Lactococcus lactis* was found to possess many plasmids coding for natural defense mechanisms against bacteriophages. Over 40 plasmids with phage defense barriers have been identified. Phage resistance systems are classified into three groups based on their mode of action: blocking of phage adsorption, restriction/modification and abortive infection. Phage-resistant *Lactococcus lactis* strains have been constructed by introducing these natural plasmids into phage-sensitive strains (Sanders, M. E., et al., Appl. Environ. Microbiol. 40:500–506 (1980)). The conjugative abilities of some of these plasmids was exploited to construct such resistant strains (Harrington, A., et al., Appl. Environ. Microbiol. 57:3405–3409 (1991); Jarvis, A. W., et al., Appl. Environ. Microbiol. 55:1537–1543 (1988); Sanders, M. E., et al., Appl. Environ. Microbiol. 52:1001–1007 (1986); and Ward, A. C., et al., J. Dairy Sci. 75:683–691 (1992)). However, after considerable industrial use of these strains, new phages capable of overcoming the introduced defense mechanism have emerged (Alatossava, T., et al., Appl. Environ. Microbiol. 57:1346–1353 (1991); Hill, C., et al., J. Bacteriol. 173:4363–4370 (1991); and Moineau, S., et al., Appl. Environ. Microbiol. 59:197–202 (1993)). Thus, the search for different natural phage barriers is still an ongoing objective for dairy product starter culture manufacturers.

Over the years several studies have established the heterologous nature of the lactococcal phage population (Jarvis, A. W., et al., Intervirology 32:2–9 (1991)). Based on electron microscopy and DNA hybridization studies, the Lactococcal and Streptococcal Phage Study Group, which is part of the International Committee on Taxonomy of Viruses, reported the existence of 12 different lactococcal phage species. Recently, this number has been reduced to 10 due to the reclassification of the 1483 and T187 species into the P335 species. Strong DNA homology is observed among members of the same species but no homology is found between species (Braun, V., et al., J. Gen. Microbiol. 135:2551–2560 (1989); Jarvis, A. W., et al., Intervirology, 32:2–9 (1991); Moineau, S., et al., Can. J. Microbiol. 38:875–882 (1992); Powell, I. A., et al., Can. J. Microbiol. 35:860–866 (1989); and Prevots, F., et al., Appl. Environ. Microbiol. 56:2180–2185 (1990)). Although many species have been isolated, only three appear to be the most problem for the dairy industry. The species 936 (small isometric head) and c2 (prolate head) have been, by far, the most disturbing lactococcal phage species worldwide. Interestingly, phages from the P335 species (small isometric head) are now being isolated with increasing frequency from North American dairy plants (Moineau, S., et al., Appl. Environ. Microbiol. 59:197–202 (1993)). Two recent surveys revealed that 100% of the 45 lactococcal phages isolated from Canadian cheese plants and U.S. buttermilk plants were classified within one of these three species: 22 phages belonged to the 936 species, 18 to the c2 species and 5 to the P335 species (Moineau, S., et al., J. Dairy Sci. 77:18 suppl. 1 (1994); and Moineau, S., et al., Can. J. Microbiol. 38:875–882 (1992)). Therefore from a practical point of view, industrial *Lactococcus lactis* strains should at least be resistant to the three most common phage species: 936, c2 and P335. Due to the diversity of lactococcal phages, the need for phage defense mechanisms with broad activity (attacking many species) is becoming more meaningful. Because of the characteristics of phages, restriction/modification (R/M) systems have the potential to fulfill this objective.

The phenomenon of R/M was first reported more than 40 years ago (Luria, S. E., et al., J. Bacteriol. 64:557–569 (1952)) and received a molecular explanation ten (10) years later (Bickle, T. A., et al., Microbiol. Rev. 57:434–450 (1993); and Dussoix, D., et al., J. Mol. Biol. 5:37–49 (1962)). The main biological activity of R/M is believed to be in preventing the entrance of foreign DNA (including phage DNA) into the cell. These gatekeepers are roughly the prokaryotic equivalent of the immune system (Wilson, G. G., Nucleic Acids Res. 19:2539–2566 (1991)). There are currently more than 2400 known restriction enzymes and over 100 have been cloned and sequenced (Raschke, E., GATA 10:49–60 (1993); and Roberts, R. J., et al., Nucleic Acid Res. 21:3125–3137 (1993)). There are several kinds of R/M systems and they appear to have equivalent biological activities but achieved in different ways. At least four types of R/M systems have been identified: I, II, IIs, and IIII (Bickle, T. A., et al., Microbiol. Rev. 57:434–450 (1993);

Wilson, G. G., Nucleic Acids Res. 19:2539–2566 (1991); and Wilson, G. G., et al., Annu. Rev. Genet. 25:585–627 (1991)). Of these, type II is the simplest and the most common. Illustrative patents are European Patent Application 0 316 677, European Patent Application 0 452 224, U.S. Pat. Nos. 4,530,904 to Hershberger, et al, 4,883,756 to Klaenhammer et al, 4,931,396 to Klaenhammer et al and 5,019,506 to Daly et al.

Many R/M systems have been characterized at the protein level. Restriction enzymes are very dissimilar, suggesting an independent evolution and not from a common ancestor (Bickle, T. A., et al., Microbiol. Rev. 57:434–450 (1993); Wilson, G. G., Nucleic Acids Res. 19:2539–2566 (1991); and Wilson, G. G., et al., Annu. Rev. Genet. 25:585–627 (1991)). In contrast, extensive similarities occur among the methyltransferases (Bickle, T. A., et al., Microbiol. Rev. 57:434–450 (1993); Klimasauskas, S., et al., Nucleic Acids Res. 17:9823–9832 (1989); Lauster, R., J. Mol. Biol. 206:313–321 (1989); McClelland, M., et al., Nucleic Acids Res. 20:2145–2157 (1992); Wilson, G. G., Nucleic Acids Res. 19:2539–2566 (1991); and Wilson, G. G., et al., Annu. Rev. Genet. 25:585–627 (1991)). They can be grouped into three classes corresponding to the modification types: $m^4C$, $m^5C$ and $m^6A$ (Wilson, G. G., Nucleic Acids Res. 19:2539–2566 (1991); and Wilson, G. G., et al., Annu. Rev. Genet. 25:585–627 (1991)). $m^4C$ and $m^6A$ can be further divided in two ($\alpha$ and $\beta$) and three ($\alpha$, $\beta$, and $\gamma$) subclasses respectively, based on their amino acid sequences (Klimasauskas, S., et al., Nucleic Acids Res. 17:9823–9832 (1989); and Lauster, R., J. Mol. Biol. 206:313–321 (1989)).

A number of plasmids encoding for R/M have been identified in Lactococcus (Hill, C., FEMS Microbiol. Rev. 12:87–108 (1993)). Surprisingly, only a handful have been partially characterized. The LlaI R/M system encoded on the conjugative plasmid pTR2030, isolated from *Lactococcus lactis* subsp. *lactis* ME2, was the first analyzed at the sequence level (Hill, C., et al., J. Bacteriol. 173:4363–4370 (1991)). The methylase gene of pTR2030 system has been sequenced and the deduced protein was found to share similarities with the type-IIs methyltransferase ($m^6A$), M. FokI (Hill, C. L., et al., J. Bacteriol. 173:4363–4370 (1991)). The endonuclease genes have also been sequenced and four open reading frames were identified (O'Sullivan, D. J., et al., FEMS Microbiol. Rev. 12:P100 (1993)). Recent data have provided evidence for a new class of multisubunit endonucleases (O'Sullivan, D. J., et al., FEMS Microbiol. Rev. 12:P100 (1993)). The restriction complex, however, has yet to be purified and its recognition sequence is unknown.

ScrFI was the first classical type II restriction enzyme isolated from *Lactococcus lactis* and is the only one commercially available (Fitzgerald, G. F., et al., Nucleic Acid Research. 10:8171–8179 (1982)). ScrFI recognizes the sequence 5'-CCNGG-3' where N is any of the nucleotide. Two methylase genes from the *Lactococcus lactis* subsp. *lactis* UC503 chromosome have been cloned and sequenced (Davis, R., et al., Appl. Environ. Microbiol. 59:777–785 (1993); and Twomey, D. P., et al., Gene 136:205–209 (1993)). They both coded for a $m^5C$ MTase. The endonuclease gene has yet to be identified. Mayo et al (Mayo, B., et al., FEMS Microbiol. Lett. 79:195–198 (1991) isolated a type II endonuclease (also named LlaI) from *L. lactis* subsp. *lactis* NCDO497 which recognized the sequence 5'-CCWGG-3 (W is A or T) but the R/M genes have not been cloned.

Recently Nyengaard, N., et al, Gene 136, 371–372 (1993) described LlaI and LlaBI, which are type II restriction endonucleases from *Lactococcus lactis* subsp. *cremoris* W9 and W56. These endonucleases recognize DNA sequences 5'/GATC-3 and 5'-C/TRYAG3', respectively. The plasmids from these strains were transformed into a plasmid free and endonuclease negative *Lactococcus lactis* subsp. *lactis* by electroporation to produce a transformed strain which resisted phage attack. The DNA was not isolated and sequenced and the natural plasmid was used for the transformation. Further, the authors did not indicate if the plasmids encoded methyl transferase. Strains W9 and W56 were not tested.

*Streptococcus thermophilus*

Similar information on phage and phage resistance is still very limited for *Streptococcus thermophilus* despite sustained phage infections in the yogurt and Mozzarella cheese industry (Mercenier et al, Genetic engineering of lactobacilli, leuconostocs and *Streptococcus thermophilus*, In M. J. Gasson and W. M. DeVos (ed.), Genetics and biotechnology of lactic acid bacteria. Blackie Acad. Prof. Glaskow, UK p. 253–293 (1994)). Fortunately, *S. thermophilus* phages are much more closely related to each other than the *L. lactis* phages. It appears that there is only one *S. thermophilus* phage species (Mercenier et al Genetic engineering of lactobacilli, leuconostocs and *Streptococcus thermophilus*, In M. J. Gasson and W. M. DeVos (ed.), Genetics and biotechnology of lactic acid bacteria. Blackie Acad. Prof. Glaskow, UK p. 253–293 (1994)). Only very few phage defense mechanisms have been reported for *S. thermophilus*. Four chromosomally-encoded type II R/M systems have been identified in *S. thermophilus*. Solaiman and Somkuti (Solaiman, D. K. Y., et al., FEMS Microbiol. Lett. 67:261–266 (1990); and Solaiman, D. K. Y., et al., FEMS Microbiol. Lett. 80:75–80 (1991)) have isolated the endonuclease Sth134I and Sth117I which are isoschizomers of HpaII and EcoRII, respectively. Benbadis et al (Benbadis, L., et al., Appl. Environ. Microbiol. 57:3677–3678 (1991)) and Guimont et al (Guimont, C., et al., Appl. Microbiol. Biotechnol. 39:216–220 (1993)) have isolated the endonucleases sslI and Sth455I, respectively. Both are also isoschizomers of EcoRII. In addition, *S. thermophilus* might possess abortive-like phage defense mechanisms (Larbi et al. J. Dairy Res. 59:349–357 (1992)), although definitive proof has yet to be demonstrated. None of the R/M systems so far identified in *S. thermophilus* have been cloned, sequenced, or used in commercial strains for improvement of phage resistance. There is believed to be no report on improvement of phage resistance of *S. thermophilus* strains.

OBJECTS

It is therefore an object of the present invention to provide an isolated DNA encoding only restriction and modification enzymes to impart phage resistance. Further, it is an object of the present invention to provide transformation vectors and transformed bacteria incorporating the DNA which are particularly useful in the dairy industry. These and other objects will become increasingly apparent by reference to the following description and the drawings.

BRIEF DESCRIPTION OF DRAWINGS

FIGS. 4A to 4C are a nucleotide sequence of the 3-kb NruI-EcoRV fragment from pSRQ700. The deduced amino acid sequence of the 3 ORFs is presented. The putatives promoter, terminator and ribosome binding site are underlined. The first codon of each ORF is in bold. The amino acids are in single letter code.

FIGS. 5A to 5C are charts showing a comparison of the amino acids between A) M.M. LlaIIA (SEQ ID NO. 2), M.DpnII (SEQ ID NO. 5), M.MboA (SEQ ID NO. 6) and E. coli Dam (SEQ ID NO. 7) methylases; B) M.LlaIIB (SEQ ID NO. 3), DpnA (SEQ ID NO. 8), M.MboC (SEQ ID NO. 9) and M.HinfI (SEQ ID NO. 10); C) R.LlaI (SEQ ID NO. 4), R.DpnII (SEQ ID NO. 11) and R.MboI (SEQ ID NO. 12). The asterisk (*) indicates conserved amino acids. Bars show gaps in the aligned sequences.

FIG. 6 is an electrophoresis gel showing restriction patterns of ØQ1, ØQ3 and ØQ5. Lane 1 and 5, 1-kb ladder (Bethesda Research Laboratories); Lane 2, ØQ1 DNA cut with EcoRV, Lane 3, ØQ2 cut with EcoRV; Lane 4, ØQ5 cut with EcoRV; Lane 6, ØQ1 cut with MboI; Lane 7, ØQ7 cut with MboI; Lane 8, ØQ5 cut with MboI.

DESCRIPTION OF PREFERRED EMBODIMENTS

Figure 1:
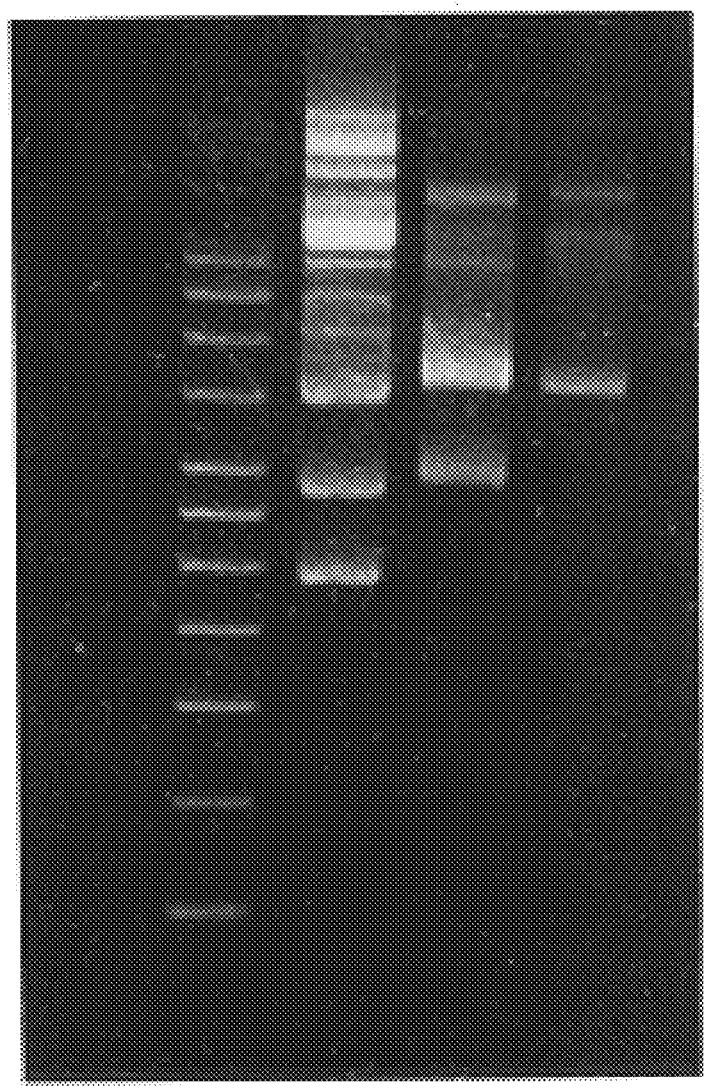
FIG. 1 is an electrophoresis gel showing a plasmid analysis of *Lactococcus lactis* strains wherein Lane 1 is supercoiled DNA ladder (GIBCO/BRL); Lane 2 is *Lactococcus lactis* DCH-4; Lane 3 is *Lactococcus lactis* SMQ-17 (pSA3 and pSRQ700); Lane 4 is *Lactococcus lactis* SMQ-16 (pSA3).

The present invention relates to an isolated DNA encoding only an enzyme which is sufficiently duplicative of a member selected from the group consisting of LlaIIA, LlaIIB and LlaIIC and mixtures thereof to restrict or modify a phage. Further the present invention relates to an isolated DNA having a nucleotide sequence essentially as set forth in SEQ ID NO. 1 selected from the group consisting of ORF1 (positions 97 to 948), ORF2 (positions 941 to 1747) and ORF3 (positions 1740 to 2651) and combinations thereof.

The present invention also relates to a recombinant plasmid containing DNA encoding an enzyme sufficiently duplicative of a member selected from the group consisting of LlaIIA, LlaIIB and LlaIIC and mixtures thereof to restrict or modify a phage.

Further the present invention relates to a bacterium harboring a recombinant plasmid containing DNA encoding for an enzyme sufficiently duplicative of a member selected from the group consisting of LlaIIA, LlaIIB and LlaIIC and mixtures thereof to restrict or modify a phage.

Further still, the present invention relates to a recombinantly produced purified protein which is an enzyme containing a sequence of amino acids sufficiently duplicative of that set forth in a member selected from the group consisting of ORF 1, ORF 2 and ORF 3 and combinations thereof in SEQ ID NO. 2, 3 or 4 such that restriction or modification of a phage can be performed with the enzyme, wherein the protein has been produced from isolated DNA of the SEQ ID NO:1. The protein can be used for assays as described hereinafter.

Further, the present invention relates to a method of imparting phage resistance to a bacterium which is sensitive to the phage which comprises incorporating recombinant DNA encoding an enzyme sufficiently duplicative of a member selected from the group consisting of LlaIIA, LlaIIB and LlaIIC and mixtures thereof into the bacterium to impart the phage resistance, wherein the DNA encoding the member is contained in strain Lactococcus lactis SMQ-17 deposited with the Agricultural Research Service Culture Collection, 1815 N. University St., Peoria, Ill. 61604, as NRRL-B-21337. Preferably the bacterium is a dairy culture. In particular, the present invention relates to a bacterium, preferably isolated and purified, selected from the group consisting of Streptococcus salivarius subsp. thermophilus and Lactococcus lactis naturally lacking in phage resistance which bacterium contains recombinant DNA encoding for an enzyme sufficiently duplicate of a member selected from the group consisting of LlaIIA, LlaIIB and LlaIIC and having a sequence of the DNA for the member is essentially as set forth in SEQ ID NO:1 to impart phage resistance.

Finally, the present invention relates to a method for fermenting a dairy product, the improvement which comprises using a dairy culture selected from the group consisting of Lactococcus lactis and Streptococcus salivarius subsp. thermophilus incorporating recombinant DNA encoding for an enzyme sufficiently duplicative of a member selected from the group consisting of LlaIIA, LlaIIB and LlaIIC to impart phage resistance, wherein the DNA for the member is contained in strain Lactococcus lactis SMQ-17 deposited as NRRL-B-21337. The DNA is generally transformed into the dairy culture.

The DNA of SEQ ID NO:1 and FIGS. 4A to 4C (Appendix I) is contained in Lactococcus lactis SMQ-17 deposited under the Budapest Treaty on Sep. 29, 1994 as NRRL-B-21337. The strain is available upon request by name and deposit number. The isolated DNA is obtained by means of EcoRV or Nru1-TcoRV digestion of pSRQ700 as described hereinafter.

The art of DNA isolation and cloning is well known to those skilled in the art. Further, the terminology of this art is well developed, see for instance EP 0316677 A2. As used herein, the term "transformed" means to transfer DNA from one bacterium to another in related bacterium. The term "recombinant" as used herein means DNA in a form not existing in nature. In general the recombinant DNA contains DNA encoding only one or more of the sequence of amino acids for LlaIIA, LlaIIB and LlaIIC as set forth in SEQ ID NO:1. The recombinant enzymes encoded are like the natural enzymes except that the physical configurations are different and they are thus different. They retain the ability to restrict or modify (methylate) the phage DNA.

Various shuttle vectors can be used. pSA3 from Dao, M., et al., Applied Environ. Microb. 49:115–119 (1985) was used.

The recombinant bacterium can be for instance Escherichia coli, a Lactococcus sp. or a Streptococcus sp. used in dairy fermentations. The E. coli are used to produce the enzymes of SEQ ID NO:2, 3 and/or 4 which can be used to produce a DNA or RNA probe in a known manner or can be used to produce antibodies to the enzymes in a well known manner for use in assays for the enzymes. Purification of the enzymes is achieved using affinity chromatography and/or molecular filtration.

The DNA of SEQ ID NO:1 can have modifications in sequence and still be homologous and still encode enzymes which have the necessary phage resistance properties. Generally within 75–100% homology is sufficient.

The preferred use of the transformed cultures containing the recombinant DNA of SEQ ID NO:1 is in dairy product fermentations. Such fermentations are well known to those skilled in the art. The preferred strains are transformed Lactococcus lactis and Streptococcus salivarius sp. thermophilus which are used in the dairy product fermentations.

EXAMPLE 1

Bacterial strains, plasmids, and media

The strains and plasmids and enzymes used in this invention are listed in Tables 1 and 2.

TABLE 1

Bacterial strains, plasmids and bacteriophages.

| Bacteria, plasmids, and phages | Relevant characteristics | Source |
|---|---|---|
| *L. lactis* subsp. *cremoris* | | |
| DCH-4 | Industrial strain, multiple plasmids, Lac$^+$ | Invention |
| UL8 | Industrial strain, host for P335 phages, Lac$^+$ | Moineau, S., et al., Can J. Microbiol. 38: 875–882 (1992) |
| SMQ-87 | UL8 (pSRQ701), Lac$^+$, Em$^r$ | Invention |
| *L. lactis* subsp. *lactis* | | |
| LM0230 | Plasmid free, host for 936 and c2 phages, Lac$^-$ | McKay, L. L., et al, Appl. Environ. Microbiol. 23:1090–1096 (1972) |
| SMQ-16 | LM0230 (pSA3), Lac$^-$, Em$^r$. | Invention |
| SMQ-17 | LM0230 (pSA3, pSRQ700), Lac$^-$, Em$^r$ | Invention |
| SMQ-39 | LM0230 (PSRQ701), Lac$^-$, Em$^r$ | Invention |
| SMQ-40 | LM0230 (pSRQ702), Lac$^-$, Em$^{rc}$ | Invention |
| SMQ-50 | LM0230 (pSRQ703), Lac$^-$, Em$^r$ | Invention |
| SMQ-117 | LM0230 (pSRQ704), Lac$^-$, Em$^r$ | Invention |
| SMQ-140 | LM0230 (pSRQ706), Lac$^-$, Em$^r$ | Invention |
| E. coli | | |
| DH5α | Transformation host | GIBCO/BRL (Grand Island, NY) |
| DMQ-149 | DH5α(pSRQ708), Apr | Invention |
| Pages | | |
| Øp2 | Small isometric headed, 936 species, 30.5 kb | L. L. McKay |
| Øsk1 | Small isometric headed, 936 species, 28.1 kb | L. L. McKay |
| Øjj50 | Small isometric headed, 936 species, 30.5 kb | J. Josephsen, et al., FEMS Microbiol. Lett. 59:161–166 (1989) |
| Øc2 | Prolate headed, c2 species, 20.7 kb | Sanders, M.E., et al., Appl. Environ. Microbiol. 40:500–596 (1980) |
| Øm13 | Prolate headed, c2 species, 20.2 kb | W. E. Sandine |
| Øeb1 | Prolate headed, c2 species, 19.6 kb | L. L. McKay |
| Øul36 | Small isometric headed, P335 species, 28.8 kb | Moineau, S., .et al., Can J. Microbiol. 38: 875–882 (1992) |
| ØQ30 | Small isometric headed, P335 species, 37.0 kb | Moineau, S., et al., J. Dairy Sci. 77:18 Suppl. 1 (1994) |
| ØQ33 | Small isometric headed, P335 species, 29.6 kb | Moineau, S., et al., J. Dairy. Sci. 77:18 Suppl. 1 (1994) |

L. L. McKay, University of Minnesota; W. E. Sandine, Oregon State University;. Lac, lactose-fermenting ability; Ap$^4$, ampicillin resistance; Cm$^r$, chloramphenicol resistance; Em$^r$, erythromycin resistance.

TABLE 2

Plasmids used in this study

| Plasmid | Relevant characteristics | Source |
|---|---|---|
| pSA3 | Shuttle vector, Cm, Tc, Em, 10.2 kb. | Dao, M.L., et al., Appl. Env.Microb. 49:115–119(1985) |
| pBS KS(+) | Cloning vector for sequencing, Ap, 2.9 kb. | Stratagene |
| pSRQ700 | Resident plasmid of DCH-4, R$^+$/M$^+$, 7.8 kb. | This study |
| pSPQ701 | 7.0-kb EcoRI fragment from pSRQ700 cloned into pSA3, R$^+$/M$^+$, Cm$^S$, Tc$^r$, Em$^r$. | This study |

TABLE 2-continued

Plasmids used in this study

| Plasmid | Relevant characteristics | Source |
| --- | --- | --- |
| pSRQ702 | 5.3-kb NcoI-EcoRI fragment from pSRQ700 cloned into pSA3, R/M$^+$, Cm$^S$, Tc$^r$, Em$^r$. | This study |
| pSRQ703 | 6 6-kb Ncol fragment from pSRQ700 cloned into pSA3, R$^+$/M$^+$, Cm$^S$, Tc$^r$, Em$^r$. | This study |
| pSRQ704 | 7.8-kb EcoRV fragment from pSRQ700 cloned into pSA3, R$^+$/M$^+$, Cm$^r$, Tc$^S$, Em$^r$. | This study |
| pSRQ706 | 3.0-kb NruI-EcORV fragment from pSRQ700 cloned info pSA3 R$^+$/M$^+$, Cm$^r$, Tc$^S$, Em$^r$. | This study |
| pSRQ708 | 3.0-kb NruI-ECORV fragment from pSRQ700 cloned into pBS, R$^+$/M$^+$, Ap$^r$. | This study |

Ap$^r$, ampicillin resistance, Cm$^r$, chloramphenicol resistance; Cm$^S$, sensitive to chloramphenicol; Em$^r$, erythromycin resistance; Tc$^r$, tetracycline resistance; Tc$^S$, tetracycline resistance; R$^+$/M$^+$, active restriction/active modification enzymes.

*Escherichia coli* was grown at 37° C. in Luria-Bertani (Sambrooke, J., et al., Molecular cloning: a laboratory manual. 2nd ed. Cold Spring Harbor Laboratory, Cold Spring Harbor, N.Y. (1989)). *Lactococcus lactis* strains were grown at 30° C. in M17 (Terzaghi, B. E., et al., Appl. Microbiol. 29:807–813 (1975)) supplemented with 0.5% glucose (GM17) or 0.5% lactose (LM17). When appropriate, antibiotics were added as follows: for *E. coli*, 50 μg/ml of ampicillin (Ap), 10 μg/ml of tetracycline (Tc), and 20 μg/ml of chloramphenicol (Cm); for *L. lactis*, 5 μg/ml of erythromycin (Em).

Bacteriophage propagation and assays

Bacteriophages used in this invention are listed in Table 1. Bacteriophages were propagated and titrated by the method of Jarvis (Jarvis, A. W., Appl. Environ. Microbiol. 36:785–789 (1978)). Efficiency of plaquing (EOP) assays were performed as described by Sanders and Klaenhammer (Sanders, M. E., et al., Appl. Environ. Microbiol. 40:500–506 (1980)). Bacteriophages c2, p2, sk1 and jj50 were supplied by T. R. Klaenhammer (North Carolina State University).

DNA Isolation and manipulation

Plasmid DNA from *E. coil* was isolated as described previously (Moineau, S., et al., Appl. Environ. Microbiol. 60:1832–1841 (1994)). Large quantities of *E. coli* plasmid DNA was isolated by using plasmid MIDI or MAXI kit (Qiagen Inc., Chatsworth, Calif.). Plasmid DNA from *L. lactis* was isolated as described by O'Sullivan and Klaenhammer (O'Sullivan, D. J., et al., Appl. Environ. Microbiol. 59:2730–2733 (1993)). Large quantity of lactococcal plasmid DNA was obtained using the Leblanc and Lee procedure (Leblanc, D. J., et al., J. Bacteriol. 140:1112–1115 (1979)) as modified by Gonzalez and Kunka (Gonzalez, C. F., et al., Appl. Environ. Microbiol. 46:81–89 (1983)). Restriction endonucleases (Gibco/BRL, Grand Island, N.Y.) and T4 DNA ligase (Boehringer Manheim, Indianapolis, Ind.) were used according to manufacturer's instructions. When needed, DNA fragments were obtained from low-melting agarose using a QIAEX gel extraction kit (Qiagen, Inc., Chatsworth, Calif.).

Electroporation

*E. col* was grown, electroporated, incubated, and plated as described previously (Moineau, S., et al., Appl. Environ. Microbiol. 60:1832–1841 (1994)). *L. lactis* was grown in GM17 supplemented with 0.5M sucrose (SGM17) and 1% glycine and electroporated as described by Holo and Nes (Holo, H., et al., Appl. Environ. Microbiol. 55:3119–3123 (1989)). The Gene Pulser apparatus (Bio-Rad Laboratories, Richmond, Calif.) was set at 25 μF and 2.45 kV, and the Pulse Controller was set at 200 Ω. Plasmid DNA was mixed with 40 μl of cells in a chilled cuvette (0.2 cm). After electroporation, *L. lactis* cells were resuspended in SGM17, incubated for 2 h at 30° C., plated on GM17 supplemented with erythromycin (5 μg/ml) and incubated for 2 days at 30° C.

Sequencing

The entire LlaII system (3 kb NruI-EcoRV fragment from pSRQ700) was cloned into *E. col* pBluescript. The resulting clone was named pSRQ708. Nested deletions were made in both orientations from pSRQ708 using the ERASE-A-BASE kit (Promega, Madison, Wis.). For the first set of deletions, the endonucleases SstI was used for protection and XbaI to start the deletion. The restriction pairs KpnI-DraII were used to obtain the nested deletions in the other orientation. Plasmid DNA was extracted from the nested clones with QIAGEN and directly used for sequencing. The sequencing reactions were performed using the DYEDEOXY TERMINATOR TAQ sequencing kit for use on the 373A automated DNA sequencing system (Applied Biosystems, Foster City, Calif.). The T7 and T3 primers were used for annealing.

Restriction enzyme purification

*L. lactis* SMQ-17 was grown in 2 L, concentrated by centrifugation (10,000 rpm, 15 min.) and washed twice in saline. The cells were then resuspended in 30 ml of PME buffer (10 mM NaH$_2$PO$_4$ pH 7.4, 0.1 mM EDTA and 10 mM β-mercaptoethanol). Cells were lysed by 15 bursts (30 seconds each followed by one minute rest) with glass beads and a bead beater (BIOSPEC, Bartlesville, Okla.). After centrifugation to remove cell debris and glass beads, the supernatant was used for ion exchange chromatography. Successive chromatographies were performed on phospho-cellulose (Whatman P11, Maidstone, England) and dimethy-laminoethyl cellulose (Whatman DE5, Maidstone, England) using a salt gradient in PME buffer. Restriction endonuclease activity was found in the fractions around 0.5 M NaCl. Lactococcal phage ul36 DNA was used as substrate and the digestions were performed at 37° C. for 2–4 h using the buffer system #2 from GIBCO/BRL (50 mM Tris-HCl pH 8.0, 10 mM MgCl$_2$, 50 mM NaCl). DNA samples were analyzed as described by Sambrooke et al in Molecular cloning: a laboratory manual, 2nd ed. Cold Spring Harbor Laboratory, Cold Spring Harbor, N.Y. (1989) in 0.7% agarose gels in TAE.

DNA and protein analysis

The DNA sequence was analyzed with DNA strider 1.2. The SwissProt database (release Jun. 29, 1994) was searched for homology to all three LlaII amino acid sequences of SEQ ID NO:1.

Isolation of pSRQ700

For many years, *Lactococcus lactis* subsp. *cremoris* DCH-4 has performed very well during the industrial buttermilk and sour cream production. One reason for continued good performance is the natural resistance of DCH-4 to lactococcal bacteriophages. One objective of this invention was to identify and transfer the DNA responsible for the phage resistance of DCH-4. The total plasmid DNA of DCH-4 was isolated and co-electroporated with the vector pSA3 into the phage sensitive-plasmid free *L. lactis*

LM0230. The latter strain was selected because it can propagate phages from two species, 936 and c2. The DNA ratio of DCH-4:pSA3 used for electroporation was about 10:1. Em-resistant colonies were tested for phage resistance by spot assay ($10^3$–$10^4$ pfu of Øp2/spot). A few phage resistant colonies were obtained, analyzed, and found to contain pSA3 and a 7.8 kb low copy plasmid which was named pSRQ700 (FIG. 1). The transformant containing pSRQ700 was named L. lactis SMQ-17 (NRRL-B-21337). Plasmid pSRQ700 was also electroporated into L. lactis UL8 which can propagate phages from the P335 species. The transformant was named L. lactis SMQ-87.

Effectiveness of pSRQ700 on lactococcal phage species

L. lactis SMQ-17 and SMQ-87 were tested for phage resistance against a total of 9 phages belonging to 3 species (3 phages/species). Phages p2, sk1 and jj50 were selected as representatives of the 936 species (Table 1). The lactococcal phage species c2 was represented by the phages c2, ml3 and eb1. These six phages were individually tested on SMQ-17 and their EOPs are presented in Table 3.

TABLE 3

Comparison between the efficiency of plaquing of lactococcal phages on L. lactis SMQ-17 and the number of MboI sites in the phage genome.

| | EOP on SMQ-17 | Number of MboI sites* |
|---|---|---|
| 936 species | | |
| øp2 | $1.7 \pm 10^{-6}$ | 11 |
| øsk1 | $2.5 \pm 10^{-6}$ | 9 |
| øjj50 | $2.0 \pm 10^{-6}$ | 10 |
| c2 species | | |
| øc2 | $1.0 \pm 10^{-4}$ | 3 |
| øml3 | $6.1 \pm 10^{-3}$ | 2 |
| øeb1 | $5.5 \pm 10^{-3}$ | 2 |
| P335 species | | |
| øul36 | $2.7 \pm 10^{-7}$ | 13 |
| øQ30 | $5.2 \pm 10^{-6}$ | 12 |
| øQ33 | $1.3 \pm 10^{-7}$ | 15 |

*Only number of fragments >0.5 kb were determined.

The new emerging P335 species was represented by the phages ul36, Q30 and Q33. They were tested separately on SMQ-87 and their EOPs are also presented in Table 3. All three 936 phages had similar EOPs in the range of $10^{-6}$. More variability was observed with the c2 species where EOPs ranged from $10^{-3}$ to $10^{-4}$. The P335 phages were the most affected by pSRQ700 since EOPs of $10^{-7}$ were observed (Table 3). Identical results were obtained when phage resistance was tested at 21, 30 and 38° C. (data not shown). These results indicated that the phage resistance mechanism encoded on pSRQ700 is temperature insensitive.

Identification of the phage resistance mechanism on pSRQ700

Phages capable of overcoming the defense mechanism encoded on pSRQ700 were isolated. These phages had EOPs of 1.0 on L. lactis SMQ-17. When these resistant (modified) phages were propagated back on their original host, they became sensitive (restricted) to pSRQ700 at the same previous level (data not shown). This temporary host specific immunity, demonstrates the presence of a classical R/M system encoded on pSRQ700. The R/M system was named LlaII.

Isolation of the restriction endonuclease

The non-specific nucleases were removed after ion exchange chromatographies performed on phosphocellulose (Whatman P11) and dimethylaminoethyl cellulose (Whatman DE5) using a salt gradient in PME (10 mM $NaH_2PO_4$ pH 7.4, 0.1 mM EDTA and 10 mM β-mercaptoethanol) buffer. DNAs from the well-characterized lactococcal phage ul36 (Moineau, S., et al., Can. J. Microbiol. 38:875–882 (1992: Moineau, S., et al., Appl. Environ. Microbiol. 59:197–202 (1993); and Moineau, S., et al., Appl. Environ. Microbiol. 60:;1832–1841 (1994)) was digested with LlaII. The digestions were conducted overnight at 37° C. since the R/M encoded on pSRQ700 is temperature-insensitive (up to 38° C.). Defined DNA fragments were identified on agarose gels (data not shown). No attempts were made to determine the number of activity units in the collected fractions nor the percentage of recovery from the crude supernatant. Unexpectedly, the restriction patterns obtained corresponded to MboI restriction patterns. Attempts to cut pSRQ700 with MboI were unsuccessful. It was concluded that the R/M system present on pSRQ700 was similar to the MboI system which recognized the sequence 5'-GATC-3' and cleaved it before the guanine.

Mapping of pSRQ700

Figure 2:
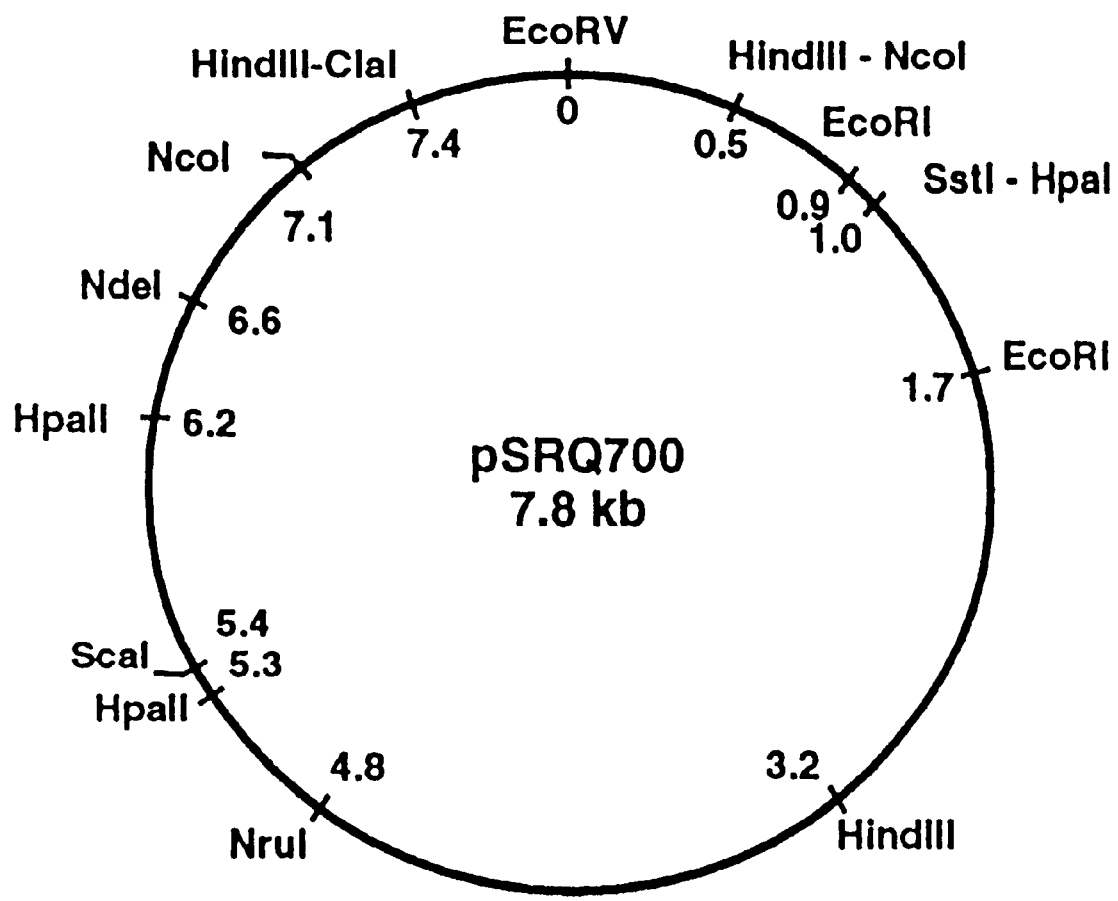
FIG. 2 is an endonuclease restriction map of lactococcal plasmid pSRQ700. Site positions are indicated in kb.

Single, double and triple digestions were performed with endonucleases to obtain a map of pSRQ700. The results are presented in FIG. 2. The following endonucleases did not cut pSRQ700: ApaI, AvaI, AvaII, BalI, BamHI, HpaI, MboI, PstI, PvuII, SalI, SmaI, SphI, XbaI, XhoI.

Localization of the LlaII system on pSRQ700

Figure 3:
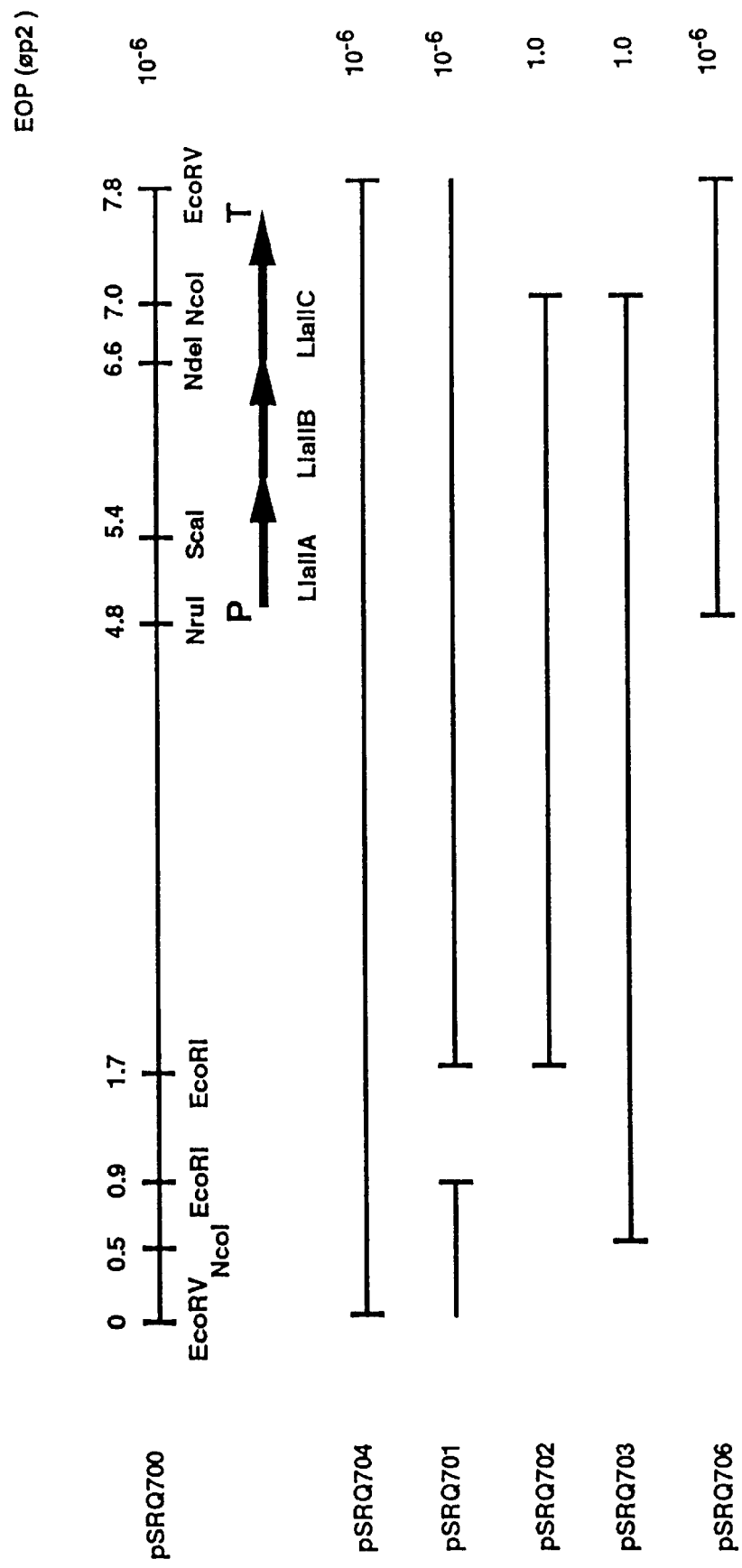
FIG. 3 is a map showing cloning of LlaII from pSRQ700 into pSA3. Clones were electroporated into LM0230. Transformants were tested for phage resistance against Øp2.

The LlaII R/M system was entirely cloned into E. coli using the E. coli-L. lactis shuttle vector pSA3 (FIG. 3). Since appropriate unique restriction sites were present on PSA3 and PSRQ700, total plasmid DNA from L. lactis SMQ-17 was directly used for cloning. Plasmid DNA from SMQ-17 was digested with selected endonucleases, phenol extracted, ethanol precipitated, ligated and the ligation mixture electroporated in E. coli DH5α. This strategy was very effective because expected clones were rapidly obtained. The clones were electroporated into L. lactis LM0230 and phage resistance was determined. The relevant clones are presented in FIG. 3. The entire R/M system of PSRQ700 was localized on a 3-kb NruI-EcoRV fragment. The PSA3 clone containing this 3 kb fragment was named pSRQ706. Similar EOPs were obtained with PSRQ700 and PSRQ706 (FIG. 3). This is due to the similar low copy number of PSA3 and PSRQ700 (FIG. 1).

DNA Sequence Analysis of the LlaII

The 3-kb NruI-EcoRV fragment containing the LlaII genes was sequenced in both directions and found to contain 2,987 bp (FIGS. 4A to 4C; SEQ ID NO:1). This fragment was 65.7% A+T rich, typical of lactococcal genes (Van de Guchte, M., et al., FEMS Microbiol. Rev. 88:73–92 (1992)). Three overlapping open reading frames (orfs) were found and the genes were named LlaIIA, LlaIIB and LlaIIC. In reference to FIGS. 4A to 4C and SEQ ID NO:1, the gene LlaIIA was localized from position 97 to position 948 and coded for a protein of 284 amino acids with an estimated weight of 33,031 Da. The gene LlaIIB was localized from position 941 to position 1747 and coded for a protein of 269 amino acids with an estimated weight of 30,904 Da. The gene LlaIIC was localized from position 1740 to position 2651 and coded for a protein of 304 amino acids with an estimated weight of 34,720 Da. Phage p2 EOP of 1.0 on L. lactis harboring pSRQ702 or pSRQ703 suggested that LlaIIC coded for the endonuclease (FIG. 3). No putative ribosome binding site (RBS) was found for LlaIIA and LlaIIB. A putative RBS (GGAG) was found preceding LlaIIC. Atypical RBS have been identified for the DpnII methylases which are similar to LlaII (FIGS. 5A to 5C). They were not found in the LlaII system. Atypical RBS may be related to translational control of the methylase gene expression (Lacks, S. A., et al., In:Genetics and Molecular Biology of Streptococci, Lactococci and Enterococci, Dunny, G. M., P. P. Cleary and L. L. McKay. (eds) ASM, Washington, D.C. p.71–76 (1991)). All three genes appear to be under the control of the same promoter. However, no definite consensus *E. coil*-10 and -35 promoter sequences could be identified. Because EOPs were the same in PSRQ700, pSRQ701 and pSRQ703 (FIG. 3), it is believed that the promoter was present in the 3.0-kb fragment. The putative promoter sequences upstream of LlaIIA is of interest. A putative -35 region was localized at position 27, followed by a 18 bp spacer, and a putative -10 region at position 51 (FIGS. 4A to 4C). A search for palindromic sequences identified two perfect inverted repeats of 19 bp, typical of a strong rho-independent terminator, at the very end of LlaIIC (FIGS. 4A to 4C). Interestingly, the stop codon of LlaIIC was within the beginning of the stemloop structure.

Protein analysis

Homology searches showed that the deduced protein coded by LlaIIA was 75.4% identical to DpnII methylase (Mannarelli, B. M., et al., Proc. Natl. Acad. Sci. 82:4468–4472 (1985)), 41.5% identical MboI methylase (Ueno, T., et al., Nucleic Acids Res. 10:2309–2313 (1993)) and 30.1% to the Dam methylase of *E. coli* (Brooks, J. E., et al., Nucleic Acids Res. 11:837–851 (1983)). It was concluded that LlaIIA codes for a methylase and was named M.LlaIIA. All three methylases (M.DpnII, M.MboA and Dam) homologous to LlaIIA are N-6 adenine methyltransferase ($m^6$A-MTases). The most conserved amino acid sequence motifs among the $m^6$A-Mtases are F-G-G (motif I) and DPPY (motif II). Their organization in the protein allowed the division of the $m^6$A-Mtases in three subclasses ($\alpha$, $\beta$ and $\gamma$). In the $m^6$A-Mtase subclass a, the motif I is found close to the N-terminal followed by a variable region of 100–200 aa and the motif II close to the C-terminal. The reverse situation is found in the subclass $\beta$, where the motif II appears before the motif I. M.LlaIIA has all the characteristics of a $m^6$A-Mtase subclass $\alpha$:F-G-G motif, a 146 aa variable region and a DPPY motif (FIG. 5). The F-G-G motif probably contained the S-adenosylmethionine binding site and DPPY might be involved in the methylation of exocyclic amino acids (Klimasauskas, S., et al., Nucleic Acids Res. 17:9823–9832 (1989)).

The deduced protein coded by LlaIIB was found to be 88.9% identical to the second methylase of DpnII (Cerritelli, S., et al., Proc. Natl. Acad. Sci. USA, 86:9223–9227 (1989)), 50.2% identical to the second methylase of MboI (Ueno, T., et al., Nucleic Acids Res. 10:2309–2313 (1993)) and 43.6% identical to the HinfI methylase (Chandrasegaran, S., et al., Gene 70:387–392 (1988)). It was concluded that LlaIIB also codes for a methylase and was named M.LlaIIB. All three methylases (M.DpnA, M.MboC and HinfI) homologous to LlaIIB are $m^6$A-Mtases but subclass $\beta$. M.LlaIIB has all the subclass $\beta$ characteristics: a DPPY motif, a 175 aa variable region and a F-G-G motif. Interestingly, FIGS. 5A to 5C also show the amino acid comparison between two sets of four $m^6$A-Mtases isolated from two Gram-positive and two Gramnegative bacteria. This enzyme methylates the same 5'-GATC-3' sequence. Despite the various origins, about 20% and 28% of the amino acids are respectively conserved in the four $\alpha$ and $\beta$ methylases studied. Interestingly, almost all tryptophan residues are conserved in the methylases studied (FIGS. 5A to 5C).

The deduced protein coded by LlaIIC was 34% and 31% identical to MboI (Ueno, T., et al., Nucleic Acids Res. 10:2309–2313 (1993)) and DpnII (de la Campa, A. G., et al., J. Biol. chem. 263:14696–14702 (1987)) endonucleases, respectively. These results confirmed that LlaIIC coded for an endonuclease and was named R.LlaII. Conserved aa motifs were observed among the three isoschizomers but their functionality is unknown.

It was thus found that *Lactococcus lactis* subsp *cremoris* DCH-4 harbors a 7.8-kb low copy plasmid (PSRQ700) coding for a temperature-insensitive R/M system similar to DpnII (Lacks, S. A., et al., In: Genetics and Molecular biology of Streptococci, Lactococci and Enterococci. Dunny, G. M., P. P. Cleary and L. L. McKay. (eds) ASM, Washington, D.C. p-71–76 (1991)) and MboI (Ueno, T., et al., Nucleic Acids Res. 10:2309–2313 (1993)). These systems recognize the non-methylated DNA sequence 5'-GATC-3' where the endonuclease cleaved before the guanine (Lacks, S. A., et al., In: Genetics and Molecular biology of Streptococci, Lactococci and Enterococci. Dunny, G. M., P. P. Cleary and L. L. McKay. (eds) ASM, Washington, D.C. p-71–76 (1991); and (Ueno, T., et al., Nucleic Acids Res. 10:2309–2313 (1993)). The plasmid PSRQ700 is probably one reason for the strong phage resistance shown by DCH-4 over the years. Any phage containing the non-methylated GATC sequence in its genome will be restricted when infecting a *L. lactis* strain containing PSRQ700.

Members of the three most common lactococcal phage species were strongly restricted by PSRQ700 as shown by their reduced EOPs (Table 3). The small isometric-headed phages of the P335 and 936 species were particularly affected by PSRQ700. This is due in part to their larger genomes. The average genome size for the P335, 936 and c2 phages used in this study was 31.8, 29.7 and 20.2-kb, respectively. However, the most important factor was the number of LlaII sites in the phage genome. Three LlaII sites in the prolate Øc2 genome were enough to restrict its EOP by 4 logs on *L. lactis* SMQ-17 (Table 3). Two LlaII sites in the Øm13 and Øeb1 genomes were still enough to reduce the EOP by 3 logs. These data are in agreement with the single hit kinetic of R/M system and shows that restriction at one site is enough to prevent phage proliferation (Wilson, G. G., et al., Annu. Rev. Genet. 25:585–627 (1991)). For the small isometric phages which had more LlaII sites in their genome, the presence of 9 to 12 sites gave a 6 log reduction in EOP, whereas 13 to 15 sites were needed for a 7 log reduction. As reported previously, the EOP decreases logarithmically as the number of sites in the phage genome increases (Wilson, G. G., et al., Annu. Rev. Genet. 25:585–627 (1991)).

Thus, phage resistance conferred by PSRQ700 was substantial against members of the 3-lactococcal phage species tested.

Close gene linkage is a feature of all R/M system and accordingly LlaII genes are adjacent (Wilson, G. G., Nucleic Acids Res. 19:2539–2566 (1991); and Wilson, G. G., et al. Annu. Rev. Genet. 25:585–627 (1991)). The LlaII system is highly related to DpnII (Lacks, S. A., et al., In:Genetics and Molecular Biology of Streptococci, Lactococci and Enterococci. Dunny, G. M., P. P. Cleary and L. L. McKay. (eds) ASM, Washington, D. C. p. 71–76 (1991)). They share the same genetic structure: two methylases followed by an endonuclease (de la Campa, A. G., et al., J. Mol. Biol. 196:457–469 (1987)). There is also gene overlapping in both systems. The most striking similarity is their methylases (Cerritelli, S., et al., Proc. Natl. Acad. Sci. USA, 86:9223–9227); and Mannarelli, B. M., et al., Proc. Natl. Acad. Sci. 82:4468–4472 (1985)). Amino acids comparison showed 75% identity between M.LlaIIA and M.DpnII and 88% between M.LlaIIB and M.DpnA (FIG. 5).

Despite the strong homology between LlaII and DpnII methylases, the endonucleases are still divergent. Only 31% of the amino acids are identical. In fact, the endonuclease of LlaII is more homologous to MboI than to DpnII. One might suggest that the methylase had a common ancestor whereas endonucleases evolved independently (Bickle, T. A., et al., Microbiol. Rev. 57:434–450 (1993); (Wilson, G. G., Nucleic Acids Res. 19:2539–2566 (1991); and Wilson, G. G., et al. Annu. Rev. Genet. 25:585–627 (1991)). Many type II R/M system appear to have formed partnerships with miscellaneous genes that were initially separated. They became linked due to a persistent selective advantage (Bickle, T. A., et al., Microbiol. Rev. 57:434–450 (1993); (Wilson, G. G., Nucleic Acids Res. 19:2539–2566 (1991); and Wilson, G. G., et al. Annu. Rev. Genet. 25:585–627 (1991)).

Finally, from a culture manufacturer standpoint, the introduction of the natural low copy number PSRQ700 into industrial *Lactococcus lactis* strains can confer strong phage resistance against phages of the 936 species and the newly emerging P335 species. Its effectiveness against c2 species will be variable. The temperature insensitivity nature of LlaII (up to 38° C.) makes this phage resistance mechanism amenable to various types of high-temperature dairy fermentations, especially cheese. The use of PSRQ700 as part of a starter rotation scheme (to avoid the build up of modified phages) can improve the overall phage resistance of starter cultures.

EXAMPLE 2

The native LlaII R/M system from *Lactococcus lactis* was expressed by and conferred strong phage resistance to various industrial *S. thermophilus* strains. Resistance was observed against phages isolated from yogurt and Mozzarella wheys.

Bacteria, bacteriophages, and media

The strains used in this study are listed in Table 4. *S. thermophilus* strains were confirmed by Rapid ID 32 Strep (BioMérieux Vitek, Inc., Hazelwood, Mo.). *Streptococcus thermophilus* strains were grown at 42° C. in GM17. When needed, antibiotics were added at 5 μg of chloramphenicol per ml. Bacteriophages used in this study are listed in Table 4.

TABLE 4

Bacteria and bacteriophages used in this study.

| Bacteria or phage | Relevant characteristics[a] | Source |
|---|---|---|
| *E.coli* | | |
| DH5α | Transformation host. | Gibco/BRL |
| *L. lactis* | | |
| LM0230 | Plasmid-free, Lac⁻, host for øp2. | 38 |
| SMQ-17 | LM0230(pSRQ700). | This Invention |
| SMQ-151 | LM0230(pSRQ707), Cm$^r$. | This Invention |
| *S. thermophilus* | | |
| SMQ-119 | Industrial strain used in yogurt, host for øQ1 and øQ3. | This Invention |
| SMQ-146 | SMQ-119(PNZ123), Cm$^r$. | This Invention |
| SMQ-154 | SMQ-119(pSRQ707), Cm$^r$. | This Invention |
| SMQ-173 | Industrial strain used for Mozzarella, host for øQ5. | This Invention |
| SMQ-174 | Industrial strain used for Mozzarella, host for øQ6. | This Invention |
| SMQ-211 | SMQ-173(pSRQ707), Cm$^r$. | This Invention |
| SMQ-212 | SMQ-174(pSRQ707), Cm$^r$. | This Invention |
| Phages | | |
| øp2 | *L. lactis* phage, small isometric-head, 936 species. | L.L. McKay |
| øQ1 | *S. thermophilus* phage isolated from yogurt. | This Invention |
| øQ3 | *S. thermophilus* phage isolated from yogurt. | This Invention |
| øQ5 | *S. thermophilus* phage isolated from Mozzarella whey. | This Invention |
| øQ6 | *S. thermophilus* phage isolated from Mozzarella whey. | This Invention |

L.L. McKay, University of Minnesota; Cm$^r$, chloramphenicol resistance; Lac⁻, deficient in lactose fermenting ability.

Streptococcal phages were propagated by the method of Jarvis et al (Jarvis, A. W., et al., Intervirology 32:2–9 (1991)). EOP assays on *S. thermophilus* hosts were performed as follows: strains were grown in GM17 overnight at 37° C., 500 μl of cells and 100 μl of diluted phages were mixed with 2.5 ml of soft agar (GM17 supplemented with 10 mM CaCl$_2$) and layered onto bottom agar (GM17+CaCl$_2$). Plates were incubated overnight 42° C. in an anaerobic jar (BBL GasPaK Plus, Beckton Dickinson, Cockeysville, Md.).

DNA isolation and manipulation

Plasmid DNA from *S. thermophilus* was isolated by using the method of O'Sullivan and Klaenhammer (O'Sullivan, D. J., et al., Appl. Environ. Microbiol. 59:2730–2733 (1993) Phage DNA was isolated as described previously (Moineau, S., et al., Appl. Environ. Microbiol. 60:1832–1841 (1994)).

Electroporation

*S. thermophilus* cells were electroporated as follows: cells were grown in GM17 until mid-exponential phase, centrifuged, washed twice with SG buffer (0.5M sucrose and 10% glycerol) and put on ice until use. Plasmid DNA (1 μg) was mixed with 40 μl of cells in a chilled Gene Pulser cuvette (0.2 cm). The Gene Pulser apparatus (Bio-Rad Laboratories, Richmond, Calif.) was set at 25 μF and 2.45 kV, and the Pulse Controller at 200 Ω. After electroporation, the *S. thermophilus* cells were immediately resuspended in the rescue broth used for *L. lactis* cells (Hill, C., FEMS Microbiol. Rev. 12:87–108 (1993)) and incubated for 2 hours at 42° C. before they were plated on GM17 supplemented with the appropriate antibiotic.

Phage isolation

Phages ØQ1 and ØQ3 were recently isolated from yogurt samples whereas ØQ5 and ØQ6 were isolated also in our laboratory but from Mozzarella whey samples. Phages ØQ1 and ØQ3 were then propagated on *S. thermophilus* SMQ-119, ØQ5 on SMQ-173 and ØQ6 on SMQ-174. The genomic DNAs of these streptococcal phages were compared after digestion with EcoRV and MboI (FIG. 6). All four *S. thermophilus* phages had different restriction patterns (FIG. 6) and consequently they were different.

Expression of LlaII in *Streptococcus thermophilus*

Figure 7:
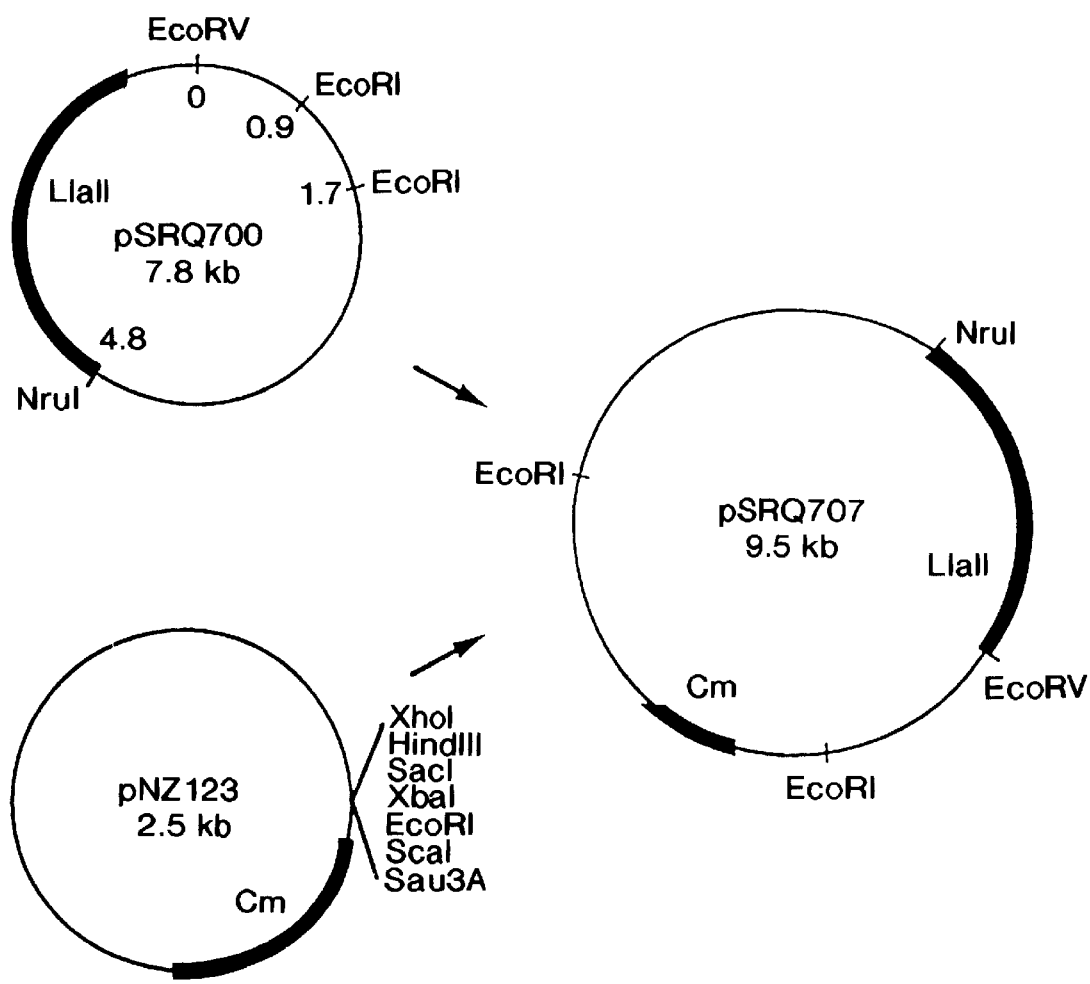
FIG. 7 is a schematic flow sheet showing the construction of the plasmids used in this study.

To verify if LlaII system could be functional in *S. thermophilus*, the LlaII genes were cloned into a vector with an origin of replication functional in *L. lactis* and *S. thermophilus*. The lactic acid bacteria shuttle vector pNZ123 (2.5 kb) (DeVos, W. M., FEMS Microbiol. Rev. 46:281–295 (1987)) was selected. A 7.0-kb EcoRI fragment from pSRQ700 was cloned into the unique EcoRI site of pNZ123 (FIG. 7). The ligation mixture was electroporated directly into the phage sensitive strain *L. lactis* LM0230. Cm-resistant transformants were obtained and tested for resistance to Øp2. A phage-resistant transformant thus obtained was named SMQ-151. The resulting pNZ123 clone containing the 7.0 kb fragment from pSRQ700 was named pSRQ707. This plasmid was electroporated into *S. thermophilus* SMQ-119 and a Cm$^r$-transformant was named SMQ-154. This clone was tested for resistance against two *S. thermophilus* phages (ØQ1 and ØQ3). Both phages were severely restricted on SMQ-154 since they had EOPs of $10^{-8}$ (Table 5).

TABLE 5

Efficiency of Plaquing of *S. thermophilus* phages on various hosts.

| Phage/Host | EOP |
| --- | --- |
| ØQ1/SMQ-119 | 1.0 |
| ØQ1/SMQ-146 | 1.0 |
| ØQ1/SMQ-151 | $2.4 \times 10^{-8}$ |
| ØQ3/SMQ-119 | 1.0 |

TABLE 5-continued

Efficiency of Plaquing of *S. thermophilus* phages on various hosts.

| Phage/Host | EOP |
| --- | --- |
| ØQ3/SMQ-151 | $6.1 \times 10^{-8}$ |
| ØQ5/SMQ-173 | 1.0 |
| ØQ5/SMQ-211 | $3.9 \times 10^{-6}$ |
| ØQ6/SMQ-174 | 1.0 |
| ØQ6/SMQ-212 | $1.2 \times 10^{-5}$ |

Plasmid pSRQ707 was also electroporated into *S. thermophilus* SMQ-173 and SMQ-174 which are commercially used for Mozzarella cheese production. Transformants were obtained for both strains, and named SMQ-211 and SMQ-212, respectively. Both transformants were tested for phage resistance. Phage Q5 had an EOP of $10^{-6}$ on SMQ-211 whereas ØQ6 and an EOP of $10^{-5}$ on SMQ-212 (Table 5). The phage resistance observed against Mozzarella phages was slightly weaker than with the yogurt phages, but still significant. These results show that the LlaII R/M system is functional in various *S. thermophilus* strains and can confer strong phage resistance in this lactic acid bacteria. This is the first report of increased phage resistance in *S. thermophilus*.

Thus, in general the present invention relates to an isolated and purified *Streptococcus thermophilus* naturally lacking in at least one phage resistance and containing recombinant DNA encoding an endonuclease from a *Lactococcus lactis* to impart the phage resistance.

Further, it relates to a method for fermenting a dairy product, the improvement which comprises using a dairy culture of *Streptococcus thermophilus* lacking in at least one phage resistance for the fermentation incorporating recombinant DNA encoding an endonuclease of *Lactococcus lactis* to impart the phage resistance.

Still further, it relates to a method of imparting phage resistance to a *Streptococcus thermophilus* which is lacking in at least one phage resistance which comprises incorporating recombinant DNA encoding an endonuclease of *Lactococcus lactis* into the *Streptococcus thermophilus* to impart the phage resistance.

The foregoing description is only illustrative of the present invention and the present invention is limited only by the hereinafter appended claims.

We claim:

1. In a method for fermenting a dairy product, the improvement which comprises using a dairy culture selected from the group consisting of *Lactococcus lactis* and *Streptococcus salivarius* subsp. *thermophilus* containing recombinant DNA encoding an enzyme a member selected from the group consisting of LlaIIA, LlaIIB, LlaIIC and combinations thereof to impart phage resistance, wherein the DNA for the member is contained in strain *Lactococcus lactis* SMQ-17 deposited as NRRL-B-21337.

2. The method of claim 1 wherein the DNA is in a vector which was used to transform the culture.

3. In a method for fermenting a dairy product, the improvement which comprises using a dairy culture of *Streptococcus salivarius* subsp. *thermophilus* containing recombinant DNA encoding at least one enzyme of *Lactococcus lactis* selected from the group consisting of LlaIIA, LlaIIB, LlaIIC, as set forth in SEQ ID NOS. 2, 3 and 4, and combinations thereof to impart phage resistance.

4. The method of claim 3 wherein the DNA is in a vector which was used to transform the culture.

5. The method of claim 1 wherein the DNA is selected from the group consisting of ORF1 (positions 97 to 948), ORF2 (positions 941 to 1747), ORF3 (positions 1740 to 2651) of FIG. 4 (SEQ ID NO:1) and combinations thereof.

6. The method of claim 2 wherein the DNA is selected from the group consisting of ORF1 (positions 97 to 948), ORF2 (positions 941 to 1747), ORF3 (positions 1740 to 2651) of FIG. 4 (SEQ ID NO:1) and combinations thereof.

7. The method of claim 1 wherein the DNA encodes LlaIIA and the DNA has a nucleotide sequence as set forth in nucleotides 97 to 948 of SEQ ID NO:1.

8. The method of claim 3 wherein the DNA encodes the enzyme LlaIIA and the DNA has a nucleotide sequence as set forth in nucleotides 97 to 948 of SEQ ID NO.1.

9. The method of claim 1 wherein the DNA encodes the enzyme LlaIIB and the DNA has a nucleotide sequence as set forth in nucleotides 941 to 1747 of SEQ ID NO.1.

10. The method of claim 3 wherein the DNA encodes the enzyme LlaIIB and the DNA has a nucleotide sequence as set forth in nucleotides 941 to 1747 of SEQ ID NO.1.

11. The method of claim 1 wherein the DNA encodes an enzyme LlaIIC and the DNA has a nucleotide sequence as set forth in nucleotides 1740 to 2651 of SEQ ID NO:1.

12. The method of claim 3 wherein the DNA encodes an enzyme LlaIIC and the DNA has a nucleotide sequence as set forth in nucleotides 1740 to 2651 of SEQ ID NO.1.

13. The method of any one of claims 1, 5, 7, 9 and 11 wherein the DNA is in a plasmid.

14. The method of any one of claims 3, 6, 8, 10 or 12 wherein the DNA is in a plasmid.

* * * * *

UNITED STATES PATENT AND TRADEMARK OFFICE
CERTIFICATE OF CORRECTION

PATENT NO. : 5,925,388　　　　　　　　　　　　Page 1 of 2
DATED : July 20, 1999
INVENTOR(S) : Sylvain Moineau, Shirley A Walker, Ebenezer R. Vedamuthu and Peter A. Vandenbergh It is certified that error appears in the above-identified patent and that said Letters Patent is hereby corrected as shown below:

Column 7, line 22, "$Em^{rc}$" should be --$Em^r$--.

Column 7, Table 1, line 29, "Apr" should be --$Ap^r$--.

Column 7, Table 1, line 30, "Pages" should be --Phages--.

Column 7, Table 1, line 40, "500-596" should be --500-506--.

Column 7, Table 1, line 55, "$Ap^4$" should be --$Ap^r$--.

Column 9, Table 2, line 7, "$R/M^+$" should be --$R^-/M^+$--.

Column 9, Table 2, line 8, "6 6-kb" should be --6.6-kb--.

Column 9, Table 2, line 8, "$R^+/M^+$" should be --$R^-/M^+$--.

Column 9, line 10, "Nrul-EcORV" should be --Nrul-EcoRV--.

Column 9, line 10, "info" should be --into--.

Column 9, line 11, "Nrul-ECORV" should be --Nrul-EcoRV--.

Column , line 13, "$AP^r$" should be --$Ap^r$--.

Column 9, line 14, "$Tc^s$, tetracycline resistance" should be --$Tc^s$, tetracycline sensitive--.

Column 9, line 54, "E. col" should be --E. coli--.

UNITED STATES PATENT AND TRADEMARK OFFICE
CERTIFICATE OF CORRECTION

PATENT NO. : 5,925,388
DATED : July 20, 1999
INVENTOR(S) : Sylvain Moineau, Shirley A. Walker, Ebenezer R. Vedamuthu and Peter A. Vandenbergh It is certified that error appears in the above-identified patent and that said Letters Patent is hereby corrected as shown below:

Column 10, line 17, "*E. col*" should be --*E. coli*--.

Column 11, Table 3, "±" (all occurrences), should be --X--.

Column 12, line 9, "60:;1832-1841" should be --60:1832-1841--.

Column 16, line 41, before "L. L. McKay" insert --$^a$-- (as the footnote indicator).

Column 16, line 55, "after "(1993)" insert --).--.

Column 18, line 19, "⌀Q6 and an EOP" should be --⌀Q6 had an EPO--.

Signed and Sealed this

Eleventh Day of January, 2000

Attest:

Q. TODD DICKINSON

*Attesting Officer*   *Acting Commissioner of Patents and Trademarks*

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 2987 base pairs
      (B) TYPE: Nucleic Acid
      (C) STRANDEDNESS: Double
      (D) TOPOLOGY: Linear (ii) MOLECULE TYPE:

(xi) SEQUENCE DESCRIPTION: SEQ ID NO:1:

```
TCGCGAGCTT TCTAATGCTT AGTGCTTTAA GATTAGGATA GCACGACTTA        50

TTTATTTTCC AATGAAATTA ACTAGCAATT CGGGTATAAT ATATTTATGA       100
```

```
ATTTATTACA AAAAAACAAG ATCAACTTAC GTCCGTTTAC TAAATGGACA      150

GGTGGGAAAA GGCAACTACT GCCACACATT CAATACCTAA TGCCAGAAAA      200

ATACAATCAT TTTTTCGAAC CTTTTATTGG TGGTGGCGCT TTGTTTTTTG      250

AACCCGCTCC TCAAAAAGCA GTTATTAACG ACTTCAATTC TGAGCTTATA      300

AACTGTTACC GGCAGATGAA AGATAATCCT GAGCAATTGA TAGAATTGTT      350

GACTAATCAT CAGCGGGAAA ATTCTAAAGA ATATTATTTA GACTTACGTT      400

CTTCTGATAG AGATGGAAGA ATTGATAAGA TGAGCGAAGT TGAACGTGCT      450

GCTAGAATTA TGTATATGCT ACGTGTTGAT TTTAATGGTT TATATCGTGT      500

TAATTCGAAA AACCAGTTTA ATGTGCCTTA TGGAAGATAT AAAAATCCTA      550

AGATAGTTGA TAAAGAATTG ATTGAAAGTA TTTCCGAGTA CTTGAATAAC      600

AATTCTATTA AGATCATGAG TGGAGATTTT GAAAAAGCCG TTAAAGAAGC      650

ACAGGATGGA GATTTTGTTT ATTTCGACCC TCCATACATT CCACTTTCTG      700

AAACTAGCGC CTTTACTTCT TATACACACG AAGGCTTTAG CTACGAAGAT      750

CAAGTTAGGC TAAGAGATTG TTTCAAACAG TTAGATTCAA AAGGGGTATT      800

CGTCATGCTT TCAAATTCTT CAAGCCCTTT AGCGGAGGAA TTATATAAAG      850

ATTTTAACAT CCATAAAATT GAAGCTACTC GAACAAATGG GGCTAAATCA      900

TCTAGTCGTG GAAAAATCAC TGAAATCATC GTAACCAATT ATGGCAATTA      950

ACGAATATAA GTATGGAGGT GTTTTAATGA CAAAACCATA CTATGAAAAA     1000

GAAAACGCAA TTCTCGTTCA CGCAGATTCA TTTAAATTAT TAGAAAAAAT     1050

TAAACCTGAA AGCATGGACA TGATATTTGC TGACCCTCCT TACTTTTTAA     1100

GTAATGGAGG AATGTCAAAT TCAGGTGGTC AAATTGTTTC TGTTGATAAA     1150

GGGGATTGGG ATAAAATTTC TTCATTTGAA GAAAAACATG ACTTTAATAG     1200

ACGTTGGATT AGGTTAGCAA GATTGGTTTT AAAACCCAAC GGAACTATTT     1250

GGGTTTCCGG AAGCCTTCAT AACATATATT CTGTCGGGAT GGCGCTGGAA     1300

CAGGAAGGTT TCAAAATCTT AAATAATATA ACTTGGCAAA AGACAAATCC     1350

TGCACCTAAT CTATCATGTC GGTACTTCAC CCACTCTACA GAGACAATTT     1400

TATGGGCAAG AAAGAACGAT AAAAAATCTC GCCATTATTA TAACTATGAA     1450

TTGATGAAAG AGTTTAATGA CGGGAAACAA ATGAAAGATG TTTGGACAGG     1500

TAGTCTGACA AAAAAATCAG AAAAATGGGC TGGGAAACAT CCAACTCAGA     1550

AGCCAGAGTA TATTTTAGAA CGGATAATCT TAGCTAGTAC AAAGGAAAAT     1600

GATTATATTT TAGACCCTTT CGTCGGAAGT GGAACTACTG GTGTAGTAGC     1650

CAAGAGATTG GGGCGTAAAT TTATTGGGAT TGATTCTGAG AAAGAATATC     1700

TTAAAATTGC TAAAAAAAGG CTAAATAAAG GAGCAACATA TGGACTTTAA     1750

TAATTACATC GGTTTAGAAT CTGACGATAG ATTAAATGCT TTTATGGCAA     1800

CACTTTCCGT AACTAATAGA ACTCCCGAAT ACTACGTGAA CTGGGAAAAA     1850

GTTGAACGTG AAACACGAAA ATTTGAATTA GAACTAAATA CTTTAAACTA     1900

TCTCATTGGG AAAGAAGATA TTTATAGTGA AGCACTTGAA CTATTTACCA     1950

ATCAACCTGA ATTGCTTAAA GCTATTCCTA GTTTGATTGC TAGTAGAGAT     2000

ACATCTTTAG ATATACTAAA CATTGACGAA AATGATGATA TGAGTTTTGA     2050

ACAACTTAAC TTTCTTGTTA TCGACGAAAA TTGTATCGCT GATTATGTAG     2100
```

```
ACTTTATTAA CCAGGCAGGT TTACTAGATT TTCTACAGAA TAAAGCAAAA      2150

CGTTCTCTGG TAGACTATGT GTATGGTGTT GAAGCAGGGC TTGATAGCAA      2200

TGCTCGAAAA AACCGAAGCG GTACAACCAT GGAGGGGATT TTAGAACGTA      2250

CTGTTTCAAA AATAGCTCAA GAGAAAGGGC TTGAATGGAA GCCACAGGCA      2300

ACCGCTTCTT TTATCAAGTC TCAATGGGAC ATAGAAGTCC CTGTAGATAA      2350

ATCAAAAAGA CGCTTTGATG CAGCAGTTTA CTCTCGTGCG CTCAATAAGG      2400

TTTGGCTCAT AGAAACAAAT TACTACGGCG GTGGAGGAAG TAAACTCAAA      2450

GCAGTTGCTG GAGAATTTAC AGAATTGAGT CAGTTTGTAA AAACATCAAA      2500

AGATAATGTT GAATTTGTAT GGGTAACAGA CGGCCAAGGG TGGAAATTTT      2550

CCCGCTTACC ACTTGCAGAA GCTTTCGGAC ACATCGATAA CGTTTTCAAT      2600

CTAACCATGT TGAAAGAAGG TTTCTTATCT GATTTATTCG AAAAAGAAAT      2650

TTAAAAAGAC AGAGAATCTC TGTCTTTTTA AATTTCAATT CCTTCCTTCT      2700

GCTAGCTATA ACTTTCCAAA AAACCTGAAA AACGGTTCTG TTGCAATTGT      2750

ATGTGGGGTC GGAACTTACT ACTATATCAT GAGAAATGAA GATTAAAGTT      2800

GAAACAAAAA AACAGATTAT TTTAAAATGT AAATCTGTTT TTGTTTGGGC      2850

TGATTTTATC ACACCAATTC TATGTTCAGA AAATGGTCAT TTTCTGGACA      2900

CTCTTCTTTT GTTATTAAAA CTCTCAAAAT CATTTACATT TATTGTTCAT      2950

TAACCCGTAA TTTATTCTAT GTTCATTTAT AGATATC                   2987
```

(2) INFORMATION FOR SEQ ID NO:2:

(i) SEQUENCE CHARACTERISTICS:
        (A) LENGTH: 284 Amino Acids
        (B) TYPE: Amino Acid
        (C) STRANDEDNESS: Single
        (D) TOPOLOGY: Linear (ii) MOLECULE TYPE: Peptide (xi) SEQUENCE DESCRIPTION: SEQ ID NO:2:

```
Met Asn Leu Leu Gln Lys Asn Lys Ile Asn Leu Arg Pro Phe Thr
                  5                  10                  15

Lys Trp Thr Gly Gly Lys Arg Gln Leu Leu Pro His Ile Gln Tyr
                 20                  25                  30

Leu Met Pro Glu Lys Tyr Asn His Phe Phe Glu Pro Phe Ile Gly
                 35                  40                  45

Gly Gly Ala Leu Phe Phe Glu Pro Ala Pro Gln Lys Ala Val Ile
                 50                  55                  60

Asn Asp Phe Asn Ser Glu Leu Ile Asn Cys Tyr Arg Gln Met Lys
                 65                  70                  75

Asp Asn Pro Glu Gln Leu Ile Glu Leu Leu Thr Asn His Gln Arg
                 80                  85                  90

Glu Asn Ser Lys Glu Tyr Tyr Leu Asp Leu Arg Ser Ser Asp Arg
                 95                 100                 105

Asp Gly Arg Ile Asp Lys Met Ser Glu Val Glu Arg Ala Ala Arg
                110                 115                 120

Ile Met Tyr Met Leu Arg Val Asp Phe Asn Gly Leu Tyr Arg Val
                125                 130                 135

Asn Ser Lys Asn Gln Phe Asn Val Pro Tyr Gly Arg Tyr Lys Asn
                140                 145                 150
```

```
Pro Lys Ile Val Asp Lys Glu Leu Ile Glu Ser Ile Ser Glu Tyr
            155                 160                 165

Leu Asn Asn Ser Ile Lys Ile Met Ser Gly Asp Phe Glu Lys
            170                 175                 180

Ala Val Lys Glu Ala Gln Asp Gly Asp Phe Val Tyr Phe Asp Pro
            185                 190                 195

Pro Tyr Ile Pro Leu Ser Glu Thr Ser Ala Phe Thr Ser Tyr Thr
            200                 205                 210

His Glu Gly Phe Ser Tyr Glu Asp Gln Val Arg Leu Arg Asp Cys
            215                 220                 225

Phe Lys Gln Leu Asp Ser Lys Gly Val Phe Val Met Leu Ser Asn
            230                 235                 240

Ser Ser Ser Pro Leu Ala Glu Glu Leu Tyr Lys Asp Phe Asn Ile
            245                 250                 255

His Lys Ile Glu Ala Thr Arg Thr Asn Gly Ala Lys Ser Ser Ser
            260                 265                 270

Arg Gly Lys Ile Thr Glu Ile Ile Val Thr Asn Tyr Gly Asn
            275                 280
```

(2) INFORMATION FOR SEQ ID NO:3:

(i) SEQUENCE CHARACTERISTICS:
        (A) LENGTH: 269 Amino Acids
        (B) TYPE:  Amino Acid
        (C) STRANDEDNESS: Single
        (D) TOPOLOGY:  Linear (ii) MOLECULE TYPE:  Peptide (xi) SEQUENCE DESCRIPTION: SEQ ID NO:3:

```
Met Ala Ile Asn Glu Tyr Lys Tyr Gly Gly Val Leu Met Thr Lys
              5                  10                  15

Pro Tyr Tyr Glu Lys Glu Asn Ala Ile Leu Val His Ala Asp Ser
             20                  25                  30

Phe Lys Leu Leu Glu Lys Ile Lys Pro Glu Ser Met Asp Met Ile
             35                  40                  45

Phe Ala Asp Pro Pro Tyr Phe Leu Ser Asn Gly Gly Met Ser Asn
             50                  55                  60

Ser Gly Gly Gln Ile Val Ser Val Asp Lys Gly Asp Trp Asp Lys
             65                  70                  75

Ile Ser Ser Phe Glu Glu Lys His Asp Phe Asn Arg Arg Trp Ile
             80                  85                  90

Arg Leu Ala Arg Leu Val Leu Lys Pro Asn Gly Thr Ile Trp Val
             95                 100                 105

Ser Gly Ser Leu His Asn Ile Tyr Ser Val Gly Met Ala Leu Glu
            110                 115                 120

Gln Glu Gly Phe Lys Ile Leu Asn Asn Ile Thr Trp Gln Lys Thr
            125                 130                 135

Asn Pro Ala Pro Asn Leu Ser Cys Arg Tyr Phe Thr His Ser Thr
            140                 145                 150

Glu Thr Ile Leu Trp Ala Arg Lys Asn Asp Lys Lys Ser Arg His
            155                 160                 165

Tyr Tyr Asn Tyr Glu Leu Met Lys Glu Phe Asn Asp Gly Lys Gln
            170                 175                 180

Met Lys Asp Val Trp Thr Gly Ser Leu Thr Lys Lys Ser Glu Lys
            185                 190                 195

Trp Ala Gly Lys His Pro Thr Gln Lys Pro Glu Tyr Ile Leu Glu
```

200                 205                 210

Arg Ile Ile Leu Ala Ser Thr Lys Glu Asn Asp Tyr Ile Leu Asp
                215                 220                 225

Pro Phe Val Gly Ser Gly Thr Thr Gly Val Val Ala Lys Arg Leu
                230                 235                 240

Gly Arg Lys Phe Ile Gly Ile Asp Ser Glu Lys Glu Tyr Leu Lys
                245                 250                 255

Ile Ala Lys Lys Arg Leu Asn Lys Gly Ala Thr Tyr Gly Leu
                260                 265

(2) INFORMATION FOR SEQ ID NO:4:

(i) SEQUENCE CHARACTERISTICS:
        (A) LENGTH: 304 Amino Acids
        (B) TYPE:   Amino Acid
        (C) STRANDEDNESS: Single
        (D) TOPOLOGY:  Linear (ii) MOLECULE TYPE:  Peptide (xi) SEQUENCE DESCRIPTION: SEQ ID NO:4:

Met Asp Phe Asn Asn Tyr Ile Gly Leu Glu Ser Asp Asp Arg Leu
                 5                  10                  15

Asn Ala Phe Met Ala Thr Leu Ser Val Thr Asn Arg Thr Pro Glu
                20                  25                  30

Tyr Tyr Val Asn Trp Glu Lys Val Glu Arg Glu Thr Arg Lys Phe
                35                  40                  45

Glu Leu Glu Leu Asn Thr Leu Asn Tyr Leu Ile Gly Lys Glu Asp
                50                  55                  60

Ile Tyr Ser Glu Ala Leu Glu Leu Phe Thr Asn Gln Pro Glu Leu
                65                  70                  75

Leu Lys Ala Ile Pro Ser Leu Ile Ala Ser Arg Asp Thr Ser Leu
                80                  85                  90

Asp Ile Leu Asn Ile Asp Glu Asn Asp Met Ser Phe Glu Gln
                95                  100                 105

Leu Asn Phe Leu Val Ile Asp Glu Asn Cys Ile Ala Asp Tyr Val
                110                 115                 120

Asp Phe Ile Asn Gln Ala Gly Leu Leu Asp Phe Leu Gln Asn Lys
                125                 130                 135

Ala Lys Arg Ser Leu Val Asp Tyr Val Tyr Gly Val Glu Ala Gly
                140                 145                 150

Leu Asp Ser Asn Ala Arg Lys Asn Arg Ser Gly Thr Thr Met Glu
                155                 160                 165

Gly Ile Leu Glu Arg Thr Val Ser Lys Ile Ala Gln Glu Lys Gly
                170                 175                 180

Leu Glu Trp Lys Pro Gln Ala Thr Ala Ser Phe Ile Lys Ser Gln
                185                 190                 195

Trp Asp Ile Glu Val Pro Val Asp Lys Ser Lys Arg Arg Phe Asp
                200                 205                 210

Ala Ala Val Tyr Ser Arg Ala Leu Asn Lys Val Trp Leu Ile Glu
                215                 220                 225

Thr Asn Tyr Tyr Gly Gly Gly Ser Lys Leu Lys Ala Val Ala
                230                 235                 240

Gly Glu Phe Thr Glu Leu Ser Gln Phe Val Lys Thr Ser Lys Asp
                245                 250                 255

Asn Val Glu Phe Val Trp Val Thr Asp Gly Gln Gly Trp Lys Phe
                260                 265                 270

```
Ser Arg Leu Pro Leu Ala Glu Ala Phe Gly His Ile Asp Asn Val
            275                 280                 285

Phe Asn Leu Thr Met Leu Lys Glu Gly Phe Leu Ser Asp Leu Phe
            290                 295                 300

Glu Lys Glu Ile (2) INFORMATION FOR SEQ ID NO:5:

(i) SEQUENCE CHARACTERISTICS:
        (A) LENGTH: 284 Amino Acids
        (B) TYPE:  Amino Acid
        (C) STRANDEDNESS: Single
        (D) TOPOLOGY:  Linear (ii) MOLECULE TYPE:  Peptide (xi) SEQUENCE DESCRIPTION: SEQ ID NO:5:

Met Lys Ile Lys Glu Ile Lys Lys Val Thr Leu Gln Pro Phe Thr
              5                  10                  15

Lys Trp Thr Gly Gly Lys Arg Gln Leu Leu Pro Val Ile Arg Glu
             20                  25                  30

Leu Ile Pro Lys Thr Tyr Asn Arg Tyr Phe Glu Pro Phe Val Gly
             35                  40                  45

Gly Gly Ala Leu Phe Phe Asp Leu Ala Pro Lys Asp Ala Val Ile
             50                  55                  60

Asn Asp Phe Asn Ala Glu Leu Ile Asn Cys Tyr Gln Gln Ile Lys
             65                  70                  75

Asp Asn Pro Gln Glu Leu Ile Glu Ile Leu Lys Val His Gln Glu
             80                  85                  90

Tyr Asn Ser Lys Glu Tyr Tyr Leu Asp Leu Arg Ser Ala Asp Arg
             95                 100                 105

Asp Glu Arg Ile Asp Met Met Ser Glu Val Gln Arg Ala Ala Arg
            110                 115                 120

Ile Leu Tyr Met Leu Arg Val Asn Phe Asn Gly Leu Tyr Arg Val
            125                 130                 135

Asn Ser Lys Asn Gln Phe Asn Val Pro Tyr Gly Arg Tyr Lys Asn
            140                 145                 150

Pro Lys Ile Val Asp Glu Glu Leu Ile Ser Ala Ile Ser Val Tyr
            155                 160                 165

Ile Asn Asn Asn Gln Leu Glu Ile Lys Val Gly Asp Phe Glu Lys
            170                 175                 180

Ala Ile Val Asp Val Arg Thr Gly Asp Phe Val Tyr Phe Asp Pro
            185                 190                 195

Pro Tyr Ile Pro Leu Ser Glu Thr Ser Ala Phe Thr Ser Tyr Thr
            200                 205                 210

His Glu Gly Phe Ser Phe Ala Asp Gln Val Arg Leu Arg Asp Ala
            215                 220                 225

Phe Lys Arg Leu Ser Asp Thr Gly Ala Tyr Val Met Leu Ser Asn
            230                 235                 240

Ser Ser Ser Ala Leu Val Glu Glu Leu Tyr Lys Asp Phe Asn Ile
            245                 250                 255

His Tyr Val Glu Ala Thr Arg Thr Asn Gly Ala Lys Ser Ser Ser
            260                 265                 270

Arg Gly Lys Ile Ser Glu Ile Ile Val Thr Asn Tyr Glu Lys
            275                 280
```

(2) INFORMATION FOR SEQ ID NO:6:

(i) SEQUENCE CHARACTERISTICS:
        (A) LENGTH: 294 Amino Acids
        (B) TYPE:  Amino Acid
        (C) STRANDEDNESS: Single
        (D) TOPOLOGY:  Linear (ii) MOLECULE TYPE:  Peptide (xi) SEQUENCE DESCRIPTION: SEQ ID NO:6:

```
Met Lys Pro Phe Ile Lys Trp Ala Gly Gly Lys Asn Ser Leu Leu
                  5                  10                  15

Asp Glu Ile Gln Lys Arg Leu Pro Asp Phe Val His Ser Gln Asp
                 20                  25                  30

Phe Cys Leu Val Glu Pro Phe Val Gly Gly Ala Val Ser Leu
                 35                  40                  45

Trp Ala Leu Ser Asp Leu Pro His Leu Lys Gln Leu Val Ile Asn
                 50                  55                  60

Asp Cys Asn Ala Asp Leu Ile Asn Val Tyr Gln Val Ile Lys Asn
                 65                  70                  75

Asn Pro Asp Asp Leu Ile Gly Tyr Ile Glu Asn Leu Gln Ser His
                 80                  85                  90

Tyr Asp Lys Leu Thr Asp Leu Glu Ser Lys Lys Pro Tyr Phe Tyr
                 95                 100                 105

His Lys Arg Asp Val Phe Asn Gln Arg Thr Ser Asn Asp Ile Glu
                110                 115                 120

Gln Ala Gly Leu Phe Ile Phe Leu Asn Lys Ser Ala Phe Asn Gly
                125                 130                 135

Leu Tyr Arg Val Asn Lys Asn Asn Gln Phe Asn Val Pro Ile Gly
                140                 145                 150

Asn Tyr Lys Lys Pro Thr Phe Val Asp Lys Glu Asn Ile Leu Asn
                155                 160                 165

Ile Ser Lys Lys Leu Gln Asn Thr Lys Ile Leu Ser Gly Asp Phe
                170                 175                 180

Glu Leu Val Leu Ala His Leu Pro Asn Asn Phe Pro Cys Leu Phe
                185                 190                 195

Tyr Leu Asp Pro Pro Tyr Arg Pro Ile Ser Asp Thr Ala Ser Phe
                200                 205                 210

Thr Ser Tyr Ser Asp Asn Gly Phe Asp Asp Asn Glu Gln Lys Arg
                215                 220                 225

Leu Ala Asn Phe Cys Lys Lys Ile Asp Lys Leu Gly His Tyr Phe
                230                 235                 240

Leu Leu Ser Asn Ser Asp Pro Lys Asn Thr Asn Ser Ser Asp Glu
                245                 250                 255

Phe Phe Asp Glu Leu Tyr Gln Asp Phe Lys Ile Glu Arg Ile Gln
                260                 265                 270

Ala Asn Arg Thr Ile Ser Ala Asn Ser Asn Gly Arg Lys Lys Val
                275                 280                 285

Asn Glu Ile Ile Val Ser Asn Gly Val
                290
```

(2) INFORMATION FOR SEQ ID NO:7:

(i) SEQUENCE CHARACTERISTICS:
        (A) LENGTH: 278 Amino Acids
        (B) TYPE:  Amino Acid
        (C) STRANDEDNESS: Single
        (D) TOPOLOGY:  Linear (ii) MOLECULE TYPE: Peptide (xi) SEQUENCE DESCRIPTION: SEQ ID NO:7:

Met Lys Lys Asn Arg Ala Phe Leu Lys Trp Ala Gly Gly Lys Tyr
                 5                  10                  15

Pro Leu Leu Asp Asp Ile Lys Arg His Leu Pro Lys Gly Glu Cys
                20                  25                  30

Leu Val Glu Pro Phe Val Gly Ala Gly Ser Val Phe Leu Asn Thr
                35                  40                  45

Asp Phe Ser Arg Tyr Ile Leu Ala Asp Ile Asn Ser Asp Leu Ile
                50                  55                  60

Ser Leu Tyr Asn Ile Val Lys Met Arg Thr Asp Glu Tyr Val Gln
                65                  70                  75

Ala Ala Arg Glu Leu Phe Val Pro Glu Thr Asn Cys Ala Glu Val
                80                  85                  90

Tyr Tyr Gln Phe Arg Glu Glu Phe Asn Lys Ser Gln Asp Pro Phe
                95                  100                 105

Arg Arg Ala Val Leu Phe Leu Tyr Leu Asn Arg Tyr Gly Tyr Asn
                110                 115                 120

Gly Leu Cys Arg Tyr Asn Leu Arg Gly Glu Phe Asn Val Pro Phe
                125                 130                 135

Gly Arg Tyr Lys Lys Pro Tyr Phe Pro Glu Ala Glu Leu Tyr His
                140                 145                 150

Phe Ala Glu Lys Ala Gln Asn Ala Phe Phe Tyr Cys Glu Ser Tyr
                155                 160                 165

Ala Asp Ser Met Ala Arg Ala Asp Asp Ala Ser Val Val Tyr Cys
                170                 175                 180

Asp Pro Pro Tyr Ala Pro Leu Ser Ala Thr Ala Asn Phe Thr Ala
                185                 190                 195

Tyr His Thr Asn Ser Phe Thr Leu Glu Gln Gln Ala His Leu Ala
                200                 205                 210

Glu Ile Ala Glu Gly Leu Val Glu Arg His Ile Pro Val Leu Ile
                215                 220                 225

Ser Asn His Asp Thr Met Leu Thr Arg Glu Trp Tyr Gln Arg Ala
                230                 235                 240

Lys Leu His Val Val Lys Val Arg Arg Ser Ile Ser Ser Asn Gly
                245                 250                 255

Gly Thr Arg Lys Lys Val Asp Glu Leu Leu Ala Leu Tyr Lys Pro
                260                 265                 270

Gly Val Val Ser Pro Ala Lys Lys
                275

(2) INFORMATION FOR SEQ ID NO:8:

(i) SEQUENCE CHARACTERISTICS:
        (A) LENGTH: 268 Amino Acids
        (B) TYPE: Amino Acid
        (C) STRANDEDNESS: Single
        (D) TOPOLOGY: Linear (ii) MOLECULE TYPE: Peptide (xi) SEQUENCE DESCRIPTION: SEQ ID NO:8:

Met Lys Asn Asn Glu Tyr Lys Tyr Gly Gly Val Leu Met Thr Lys
                5                   10                  15

Pro Tyr Tyr Asn Lys Asn Lys Met Ile Leu Val His Ser Asp Thr
                20                  25                  30

```
Phe Lys Phe Leu Ser Lys Met Lys Pro Glu Ser Met Asp Met Ile
                 35                  40                  45

Phe Ala Asp Pro Pro Tyr Phe Leu Ser Asn Gly Gly Ile Ser Asn
                 50                  55                  60

Ser Gly Gly Gln Val Val Ser Val Asp Lys Gly Asp Trp Asp Lys
                 65                  70                  75

Ile Ser Ser Phe Glu Glu Lys His Glu Phe Asn Arg Lys Trp Ile
                 80                  85                  90

Arg Leu Ala Lys Glu Val Leu Lys Pro Asn Gly Thr Val Trp Ile
                 95                 100                 105

Ser Gly Ser Leu His Asn Ile Tyr Ser Val Gly Met Ala Leu Glu
                110                 115                 120

Gln Glu Gly Phe Lys Ile Leu Asn Asn Ile Thr Trp Gln Lys Thr
                125                 130                 135

Asn Pro Ala Pro Asn Leu Ser Cys Arg Tyr Phe Thr His Ser Thr
                140                 145                 150

Glu Thr Ile Leu Trp Ala Arg Lys Asn Asp Lys Lys Ala Arg His
                155                 160                 165

Tyr Tyr Asn Tyr Asp Leu Met Lys Glu Leu Asn Asp Gly Lys Gln
                170                 175                 180

Met Lys Asp Val Trp Thr Gly Ser Leu Thr Lys Val Glu Lys
                185                 190                 195

Trp Ala Gly Lys His Pro Thr Gln Lys Pro Glu Tyr Leu Leu Glu
                200                 205                 210

Arg Ile Ile Leu Ala Ser Thr Lys Glu Gly Asp Tyr Ile Leu Asp
                215                 220                 225

Pro Phe Val Gly Ser Gly Thr Thr Gly Val Val Ala Lys Arg Leu
                230                 235                 240

Gly Arg Arg Phe Ile Gly Ile Asp Ala Glu Lys Glu Tyr Leu Lys
                245                 250                 255

Ile Ala Arg Lys Arg Leu Glu Ala Glu Asn Glu Thr Asn
                260                 265

(2) INFORMATION FOR SEQ ID NO:9:

(i) SEQUENCE CHARACTERISTICS:
        (A) LENGTH: 273 Amino Acids
        (B) TYPE:  Amino Acid
        (C) STRANDEDNESS: Single
        (D) TOPOLOGY:  Linear (ii) MOLECULE TYPE:  Peptide (xi) SEQUENCE DESCRIPTION: SEQ ID NO:9:

Met Arg Ile Lys Pro Tyr Phe Glu Ser Asp Asp Lys Asn Phe Asn
                  5                  10                  15

Ile Tyr Gln Gly Asn Cys Ile Asp Phe Met Ser His Phe Gln Asp
                 20                  25                  30

Asn Ser Ile Asp Met Ile Phe Ala Asp Pro Pro Tyr Phe Leu Ser
                 35                  40                  45

Asn Asp Gly Leu Thr Phe Lys Asn Ser Ile Ile Gln Ser Val Asn
                 50                  55                  60

Lys Gly Glu Trp Asp Lys Asn Asp Asn Glu Ala Ser Ile Tyr Asn
                 65                  70                  75

Phe Asn His Glu Trp Ile Ala Gln Ala Arg Gln Leu Leu Lys Asp
                 80                  85                  90
```

```
Asn Gly Thr Ile Trp Ile Ser Gly Thr His His Asn Ile Phe Thr
            95                  100                 105

Val Gly Gln Val Leu Lys Glu Asn Asn Phe Lys Ile Leu Asn Ile
            110                 115                 120

Ile Thr Trp Glu Lys Pro Asn Pro Pro Asn Phe Ser Cys Arg
            125                 130                 135

Tyr Phe Thr Tyr Ser Ser Glu Trp Ile Ile Trp Ala Arg Lys His
            140                 145                 150

Ser Lys Ile Pro His Tyr Phe Asn Tyr Asp Leu Met Lys Lys Leu
            155                 160                 165

Asn Gly Asp Lys Gln Gln Lys Asp Ile Trp Arg Leu Pro Ala Val
            170                 175                 180

Gly Ser Trp Glu Lys Thr Gln Gly Lys His Pro Thr Gln Lys Pro
            185                 190                 195

Leu Gly Leu Leu Ser Arg Ile Ile Leu Ser Ser Thr Gln Lys Asp
            200                 205                 210

Asp Leu Ile Leu Asp Pro Phe Ser Gly Ser Gly Thr Thr Gly Ile
            215                 220                 225

Ala Gly Val Leu Leu Asp Arg Asn Tyr Ile Gly Ile Glu Gln Glu
            230                 235                 240

Leu Glu Phe Leu Glu Leu Ser Lys Arg Arg Tyr His Glu Ile Thr
            245                 250                 255

Pro Val Leu Lys Asn Glu Phe Lys Gln Lys Ile Arg Lys Gln Ile
            260                 265                 270

Ser Ala Ile
```

(2) INFORMATION FOR SEQ ID NO:10:

(i) SEQUENCE CHARACTERISTICS:
        (A) LENGTH: 287 Amino Acids
        (B) TYPE: Amino Acid
        (C) STRANDEDNESS: Single
        (D) TOPOLOGY: Linear (ii) MOLECULE TYPE: Peptide (xi) SEQUENCE DESCRIPTION: SEQ ID NO:10:

```
Met Met Lys Glu Asn Ile Asn Asp Phe Leu Asn Thr Ile Leu Lys
             5                  10                  15

Gly Asp Cys Ile Glu Lys Leu Lys Thr Ile Pro Asn Glu Ser Ile
            20                  25                  30

Asp Leu Ile Phe Ala Asp Pro Pro Tyr Phe Met Gln Thr Glu Gly
            35                  40                  45

Lys Leu Leu Arg Thr Asn Gly Asp Glu Phe Ser Gly Val Asp Asp
            50                  55                  60

Glu Trp Asp Lys Phe Asn Asp Phe Val Glu Tyr Asp Ser Phe Cys
            65                  70                  75

Glu Leu Trp Leu Lys Glu Cys Lys Arg Ile Leu Lys Ser Thr Gly
            80                  85                  90

Ser Ile Trp Val Ile Gly Ser Phe Gln Asn Ile Tyr Arg Ile Gly
            95                  100                 105

Tyr Ile Met Gln Asn Leu Asp Phe Trp Ile Leu Asn Asp Val Ile
            110                 115                 120

Trp Asn Lys Thr Asn Pro Val Pro Asn Phe Gly Gly Thr Arg Phe
            125                 130                 135

Cys Asn Ala His Glu Thr Met Leu Trp Cys Ser Lys Cys Lys Lys
            140                 145                 150
```

```
Asn Lys Phe Thr Phe Asn Tyr Lys Thr Met Lys His Leu Asn Gln
            155                 160                 165

Glu Lys Gln Glu Arg Ser Val Trp Ser Leu Ser Leu Cys Thr Gly
            170                 175                 180

Lys Glu Arg Ile Lys Asp Glu Gly Lys Lys Ala His Ser Thr
            185                 190                 195

Gln Lys Pro Glu Ser Leu Leu Tyr Lys Val Ile Leu Ser Ser Ser
            200                 205                 210

Lys Pro Asn Asp Val Val Leu Asp Pro Phe Phe Gly Thr Gly Thr
            215                 220                 225

Thr Gly Ala Val Ala Lys Ala Leu Gly Arg Asn Tyr Ile Gly Ile
            230                 235                 240

Glu Arg Glu Gln Lys Tyr Ile Asp Val Ala Glu Lys Arg Leu Arg
            245                 250                 255

Glu Ile Lys Pro Asn Pro Asn Asp Ile Glu Leu Leu Ser Leu Glu
            260                 265                 270

Ile Lys Pro Pro Lys Val Pro Met Lys Thr Leu Ile Glu Ala Asp
            275                 280                 285

Phe Leu (2) INFORMATION FOR SEQ ID NO:11:

(i) SEQUENCE CHARACTERISTICS:
        (A) LENGTH: 288 Amino Acids
        (B) TYPE:  Amino Acid
        (C) STRANDEDNESS: Single
        (D) TOPOLOGY:  Linear (ii) MOLECULE TYPE:  Peptide (xi) SEQUENCE DESCRIPTION: SEQ ID NO:11:

Met Lys Gln Thr Arg Asn Phe Asp Glu Trp Leu Ser Thr Met Thr
              5                  10                  15

Asp Thr Val Ala Asp Trp Thr Tyr Tyr Thr Asp Phe Pro Lys Val
             20                  25                  30

Tyr Lys Asn Val Ser Ser Ile Lys Val Ala Leu Asn Ile Met Asn
             35                  40                  45

Ser Leu Ile Gly Ser Lys Asn Ile Gln Glu Asp Phe Leu Asp Leu
             50                  55                  60

Tyr Gln Asn Tyr Pro Glu Ile Leu Lys Val Val Pro Leu Leu Ile
             65                  70                  75

Ala Lys Arg Leu Arg Asp Thr Ile Ile Val Lys Asp Pro Ile Lys
             80                  85                  90

Asp Phe Tyr Phe Asp Phe Ser Lys Arg Asn Tyr Ser Ile Glu Glu
             95                 100                 105

Tyr Thr Met Phe Leu Glu Lys Ser Gly Ile Phe Asp Leu Leu Gln
            110                 115                 120

Asn His Leu Val Ser Asn Leu Val Asp Tyr Val Thr Gly Val Glu
            125                 130                 135

Val Gly Met Asp Thr Asn Gly Arg Lys Asn Arg Thr Gly Asp Ala
            140                 145                 150

Met Glu Asn Ile Val Gln Ser Tyr Leu Glu Ala Glu Gly Tyr Ile
            155                 160                 165

Leu Gly Glu Asn Leu Phe Lys Glu Ile Glu Gln Asn Glu Ile Glu
            170                 175                 180

Glu Ile Phe Ser Val Asp Leu Ser Ala Ile Thr Asn Asp Gly Asn
```

-continued

```
                185                 190                 195
Thr Val Lys Arg Phe Asp Phe Val Ile Lys Asn Glu Gln Val Leu
                200                 205                 210
Tyr Leu Ile Glu Val Asn Phe Tyr Ser Gly Ser Gly Ser Lys Leu
                215                 220                 225
Asn Glu Thr Ala Arg Ser Tyr Lys Met Ile Ala Glu Glu Thr Lys
                230                 235                 240
Ala Ile Pro Asn Val Glu Phe Met Trp Ile Thr Asp Gly Gln Gly
                245                 250                 255
Trp Tyr Lys Ala Lys Asn Asn Leu Arg Glu Thr Phe Asp Ile Leu
                260                 265                 270
Pro Phe Leu Tyr Asn Ile Asn Asp Leu Glu His Asn Ile Leu Lys
                275                 280                 285
Asn Leu Lys
```

(2) INFORMATION FOR SEQ ID NO:12:

(i) SEQUENCE CHARACTERISTICS:
        (A) LENGTH: 280 Amino Acids
        (B) TYPE:  Amino Acid
        (C) STRANDEDNESS: Single
        (D) TOPOLOGY:  Linear (ii) MOLECULE TYPE:  Peptide (xi) SEQUENCE DESCRIPTION: SEQ ID NO:12:

```
Met Lys Leu Ala Phe Asp Asp Phe Leu Asn Ser Met Ser Glu Thr
                5                   10                  15
Asn Thr Thr Leu Asp Tyr Phe Thr Asp Phe Asp Lys Val Lys Lys
                20                  25                  30
Asn Val Ala Gln Ile Glu Ile His Leu Asn Gln Leu Asn Tyr Leu
                35                  40                  45
Leu Gly Lys Asp Asp Leu Lys Gln Ala Val Tyr Asp Leu Tyr Ala
                50                  55                  60
Glu Cys Pro Asn Ala Phe Ser Ile Leu Glu Ile Leu Ile Ala Val
                65                  70                  75
Arg Lys Lys Glu Gln Lys Lys Ser Leu Asp Glu Lys Gly Gln Val
                80                  85                  90
Val Thr Leu Asn Ser Tyr Phe Gln Ser Ala Asp Lys Ile Ile Asp
                95                  100                 105
Phe Leu Asn Asn Thr Gly Leu Ala Asp Val Phe Arg Asp Lys Asn
                110                 115                 120
Ile Lys Asn Leu Val Asp Tyr Val Phe Gly Ile Glu Val Gly Leu
                125                 130                 135
Asp Thr Asn Ala Arg Lys Asn Arg Gly Gly Asp Asn Met Ser Lys
                140                 145                 150
Ala Val Gln Leu Leu Phe Asp Asn Ala Asp Ile Tyr Tyr Lys Lys
                155                 160                 165
Glu Val Arg Asn Thr Ile Phe Thr Asp Ile Glu Ser Leu Gly Ala
                170                 175                 180
Asp Val Lys Gln Phe Asp Phe Val Ile Lys Thr Lys Arg Lys Thr
                185                 190                 195
Tyr Val Ile Glu Thr Asn Tyr Tyr Asn Ser Gly Gly Ser Lys Leu
                200                 205                 210
Asn Glu Val Ala Arg Ala Tyr Thr Asp Val Ala Pro Lys Ile Asn
                215                 220                 225
```

```
Gln Tyr Ser Gln Tyr Glu Phe Val Trp Ile Thr Asp Gly Gln Gly
                230                 235                 240

Trp Lys Thr Ala Lys Asn Lys Leu Gln Glu Ala Tyr Thr His Ile
                245                 250                 255

Pro Ser Val Tyr Asn Leu Tyr Thr Leu His Gly Phe Ile Glu Gln
                260                 265                 270

Leu Asn Ser Glu Gly Val Ile Lys Asp Trp
                275             280
```